(12) United States Patent
Newmark et al.

(10) Patent No.: US 7,744,931 B2
(45) Date of Patent: *Jun. 29, 2010

(54) METHODS FOR TREATING ORAL CANCERS WITH HERBAL COMPOSITIONS

(75) Inventors: Thomas Newmark, Brattleboro, VT (US); Robert Newman, Houston, TX (US); Peiying Yang, Sugar Land, TX (US); Paul Schulick, Brattleboro, VT (US)

(73) Assignees: New Chapter Inc., Brattleboro, VT (US); Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/979,779

(22) Filed: Nov. 8, 2007

(65) Prior Publication Data

US 2008/0233218 A1    Sep. 25, 2008

Related U.S. Application Data

(63) Continuation-in-part of application No. 11/452,246, filed on Jun. 14, 2006.

(60) Provisional application No. 60/857,481, filed on Nov. 8, 2006, provisional application No. 60/690,161, filed on Jun. 14, 2005, provisional application No. 60/792,330, filed on Apr. 17, 2006.

(51) Int. Cl.
*A61K 36/00*    (2006.01)
*A61K 36/82*    (2006.01)
*A61K 36/53*    (2006.01)
*A61K 36/906*    (2006.01)

(52) U.S. Cl. .............. 424/725; 424/729; 424/745; 424/756; 424/777

(58) Field of Classification Search .............. None
See application file for complete search history.

(56) References Cited

U.S. PATENT DOCUMENTS

| | | | |
|---|---|---|---|
| 6,264,995 B1 * | 7/2001 | Newmark et al. | 424/725 |
| 6,274,177 B1 * | 8/2001 | Wu et al. | 424/756 |
| 6,387,416 B1 * | 5/2002 | Newmark et al. | 424/725 |
| 6,391,346 B1 * | 5/2002 | Newmark et al. | 424/756 |
| 6,592,896 B2 * | 7/2003 | Rosenbloom | 424/464 |
| 7,067,159 B2 * | 6/2006 | Newmark et al. | 424/725 |
| 7,070,816 B2 * | 7/2006 | Newmark et al. | 424/725 |
| 2007/0042059 A1 * | 2/2007 | Newmark et al. | 424/741 |

* cited by examiner

*Primary Examiner*—Christopher R. Tate
(74) *Attorney, Agent, or Firm*—The Nath Law Group; Jerald L. Meyer; Charles D. Niebylski

(57) ABSTRACT

The inventive subject matter relates to methods for treating oral cancers, comprising administration of a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry. The inventive subject matter further relates to methods for modulating gene expression of genes selected from the group consisting of interleukin-1α, interleukin-1β, heme oxygenase 1, aldo-keto reductase family 1, member C2, colony stimulating factor 3, leukemia inhibitory factor, heat shock 70 kDa protein, and combinations thereof, by administration of an effective amount of said compositions.

34 Claims, 9 Drawing Sheets

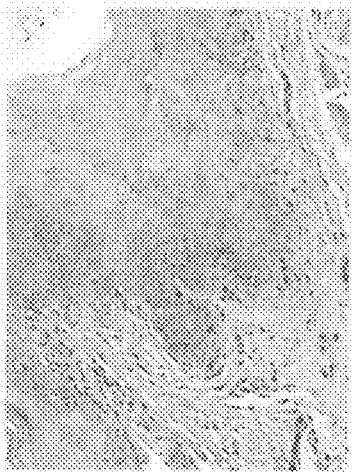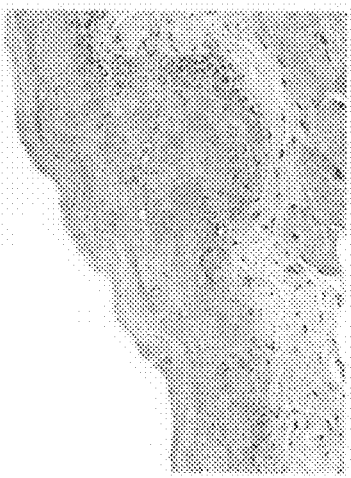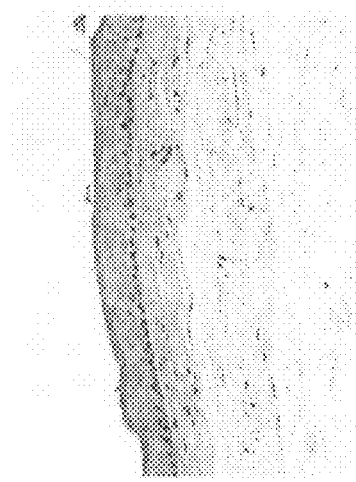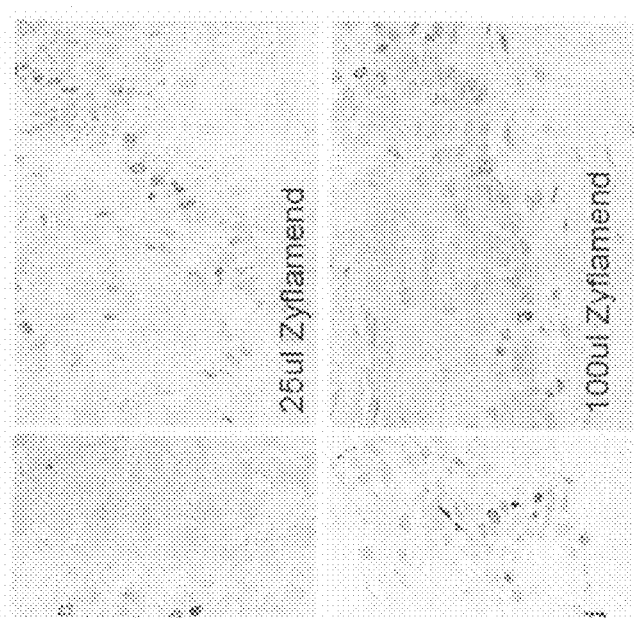
Figure 4
Figure 5

METHODS FOR TREATING ORAL CANCERS WITH HERBAL COMPOSITIONS

This application is a continuation-in-part of U.S. patent application Ser. No. 11/452,246, filed Jun. 14, 2006, which claims the benefit of U.S. Provisional Patent Applications No. 60/690,161, filed Jun. 14, 2005, and No. 60/792,330, filed Apr. 17, 2006, the contents of which are hereby incorporated by reference in their entirety. This application further claims the benefit of U.S. Provisional Patent Application No. 60/857,481, filed Nov. 8, 2006, the contents of which is hereby incorporated by reference in its entirety.

BACKGROUND OF THE INVENTIVE SUBJECT MATTER

1. Field of the Inventive Subject Matter

The inventive subject matter relates to novel methods for treating oral cancers, comprising administration of a composition comprising therapeutically effective amounts of supercritical extracts of rosemary, turmeric, oregano and ginger; and therapeutically effective amounts of hydroalcoholic extracts of holy basil, ginger, turmeric, Scutellaria baicalensis, rosemary, green tea, huzhang, Chinese goldthread, and barberry. The inventive subject matter further relates to methods for modulating expression of $LTB_4$ by administration of an effective amount of said compositions.

2. Background

Oral cancers. 30,000 Americans will be diagnosed with oral or pharyngeal cancer this year. It will cause over 8,000 deaths, killing roughly 1 person per hour, 24 hours per day. Of those 30,000 newly diagnosed individuals, only half will be alive in 5 years. This is a number which has not significantly improved in decades. The death rate for oral cancer is higher than that of cervical cancer, Hodgkin's disease, cancer of the brain, liver, testes, kidney, or skin cancer (malignant melanoma). If you expand the definition of oral cancers to include cancer of the larynx, for which the risk factors are the same, the numbers of diagnosed cases grow to 41,000 individuals, and 12,500 deaths per year in the US alone. Worldwide the problem is much greater, with over 350,000 to 400,000 new cases being found each year.

The death rate associated with this cancer is particularly high due to the cancer being routinely discovered late in its development. Often it is only discovered when the cancer has metastasized to another location, most likely the lymph nodes of the neck. Prognosis at this stage of discovery is significantly worse than when it is caught in a localized area. Besides the metastasis, at these later stages, the primary tumor has had time to invade deep into local structures. Oral cancer is particularly dangerous because it has a high risk of producing second, primary tumors. This means that patients who survive a first encounter with the disease, have up to a 20 times higher risk of developing a second cancer. This heightened risk factor can last for 5 to 10 years after the first occurrence. There are several types of oral cancers, but 90% are squamous cell carcinomas.

Understanding the causative factors of cancer will contribute to prevention of the disease. Age is frequently named as a risk factor for oral cancer, as most of the time it occurs in those over the age of 40. The age of diagnosed patients may indicate a time component in the biochemical or biophysical processes of aging cells that allows malignant transformation, or perhaps, immune system competence diminishes with age.

However, it is likely that the accumulative damage from other factors, such as tobacco use, are the real culprits. It may take several decades of smoking for instance, to precipitate the development of a cancer. Having said that, tobacco use in all its forms is number one on the list of risk factors. At least 75% of those diagnosed are tobacco users. When you combine tobacco with heavy use of alcohol, your risk is significantly increased, as the two act synergistically. Those who both smoke and drink, have a 15 times greater risk of developing oral cancer than others.

Tobacco and alcohol are essentially chemical factors, but they can also be considered lifestyle factors, since we have some control over them. Besides these, there are physical factors such as exposure to ultraviolet radiation. This is a causative agent in cancers of the lip, as well as other skin cancers. Cancer of the lip is one oral cancer whose numbers have declined in the last few decades. This is likely due to the increased awareness of the damaging effects of prolonged exposure to sunlight, and the use of sunscreens for protection. Another physical factor is exposure to x-rays. Radiographs regularly taken during examinations, and at the dental office, are safe, but remember that radiation exposure is accumulative over a lifetime. It has been implicated in several head and neck cancers.

Biological factors include viruses and fungi, which have been found in association with oral cancers. The human papilloma virus, particularly HPV16 and 18, have been implicated in some oral cancers. HPV is a common, sexually transmitted virus, which infects about 40 million Americans. There are about 80 strains of HPV, most thought to be harmless. But 1% of those infected, have the HPV16 strain which is a causative agent in cervical cancer, and now is linked to oral cancer as well. There are other risk factors which have been associated with oral cancers, but have not yet been definitively shown to participate in their development. These include lichen planus, an inflammatory disease of the oral soft tissues.

There are studies which indicate a diet low in fruits and vegetables could be a risk factor, and that conversely, one high in these foods may have a protective value against many types of cancer.

After a definitive diagnosis has been made and the cancer has been staged, treatment may begin. Treatment of oral cancers is ideally a multidisciplinary approach involving the efforts of surgeons, radiation oncologists, chemotherapy oncologists, dental practitioners, nutritionists, and rehabilitation and restorative specialists. The actual curative treatment modalities are usually surgery and radiation, with chemotherapy added to decrease the possibility of metastasis, to sensitize the malignant cells to radiation, or for those patients who have confirmed distant metastasis of the disease.

Based on 1991 National Cancer Institute Surveillance, Epidemiology, and End Results data, the overall incidence and mortality rates for oral and pharyngeal cancer combined are 10.4 per 100,000 population and 2.9 per 100,000 population, respectively. The annual incidence of 15.7 per 100,000 for males far exceeds the rate of 6.0 per 100,000 for females. (1)

Mortality rates show similar differentials: 4.5 per 100,000 per year for males, 1.7 per 100,000 per year for females. This gender difference is also evident in the lifetime risks of developing oral cancer: 1.5% for males and 0.7% for females (based on 1989-91 incidence rates).

5-lipoxygenase and 5-lipoxygenase Inhibitors. The 5-lipoxygenase (5-LO) pathway is one of at least four lipoxygenase pathways of arachidonic acid metabolism. The 5-lipoxygenase pathway consists of enzymes that regulate a series of biochemical reactions that result in the transformation of arachidonic acid to leukotriene $A_4$, which can then be further metabolized to leukotriene $B_4$ or to leukotriene $C_4$. Activation of the 5-LO pathway leads to the biosynthesis of proinflammatory leukotriene lipid mediators, while inhibition of the 5-LO pathway may have anti-inflammatory effects.

Some compounds which inhibit 5-lipoxygenase have been described in U.S. Pat. Nos. 6,653,311, 6,455,541, 6,399,105, 6,121,323, 5,342,838, 5,298,514, 5,145,861, 5,130,483, 4,933,329, and 4,731,382. Drugs such as MK-886 (3-(1-(4-chlorobenzyl)-3-tert-butyl-thio-5-isopropylindol-2-yl)-2,2-dimethyl propanoic acid), L-656,224 ((7-chloro-2-[4-methoxypentyl]methyl)-3-methyl-5-propyl-4-benzofuranol), pentacyclic triterpene acetyl-11-keto-β-boswellic acid, PF-5901, Zileuton, and tepoxalin are intended to selectively inhibit 5-lipoxygenase. However, these drugs appear to have long term side effects. There is thus a continuing need for 5-lipoxygenase inhibitors which avoid side effects associated with current compositions.

Cyclooxygenase and Cyclooxygenase Inhibitors. Cyclooxygenase is an enzyme-protein complex with a variety of biochemical actions. There are at least three primary COX isoenzymes, COX-1, COX-2, and COX-3. COX-1 is a constitutive enzyme, produced at a reasonably consistent level at all times. It plays an important role in, for example, gastrointestinal protection, kidney function, and the aggregation of blood platelets. COX-2 production is not constant; it varies depending on signals from various biochemical catalysts. For example, in the case of arthritis inflammation and pain, COX-2 responds to tissue damage by oxidizing arachidonic acid, creating prostaglandins which in turn produce local inflammation. COX-3 has been identified relatively recently (Chandrasekharan, et al., PNAS U.S.A., 99(21):13926-31 (2002)). In humans, COX-3 mRNA is expressed most abundantly in the cerebral cortex and heart tissues. COX-3 activity is selectively inhibited by analgesic/antipyretic drugs. It has been suggested that inhibition of COX-3 could represent a mechanism by which these drugs decrease pain and possibly fever.

Prostaglandins play a major role in the inflammatory process and the inhibition of prostaglandin production, especially production of $PGG_2$, $PGH_2$, and $PGE_2$, has been a common target of anti-inflammatory drug discovery. However, common non-steroidal anti-inflammatory drugs (hereinafter referred to as "NSAIDs") that are active in reducing the prostaglandin-induced pain and swelling associated with the inflammation process are also active in affecting other prostaglandin-regulated processes not associated with the inflammation process.

NSAIDs have been found to prevent the production of prostaglandins by inhibiting enzymes in the human arachidonic acid/prostaglandin pathway, including the cyclooxygenase enzymes. Traditional non-steroidal anti-inflammatory drugs, such as aspirin, work by inhibiting both COX-1 and COX-2. Thus, non-specific NSAIDs can have a damaging effect on the gastrointestinal tract, kidneys, and liver; blocking COX-1 can make the stomach lining more vulnerable, and reduced thromboxane production thins the blood, making gastrointestinal hemorrhage more likely, and may cause inadequate regulation of cellular immune functions and the secretion of various cytokines. The use of high doses of most common NSAIDs can produce severe side effects, including life threatening ulcers, that limit their therapeutic potential.

COX-2 is associated with inflammation and provides a viable target of inhibition which more effectively reduces inflammation and produces fewer and less drastic side effects. Thus, researchers have been motivated to develop selective COX-2 inhibitors to reduce inflammation and relieve pain without the gastrointestinal damage brought on by inhibiting COX-1. In addition, the current scientific understanding in the art suggests that COX-2 inhibition may serve an important function in promoting normal cell growth in the colon, pancreas, breast tissue, and other organ systems.

Some compounds which selectively inhibit cyclooxygenase-2 have been described in U.S. Pat. Nos. 5,380,738, 5,344,991, 5,393,790, 5,434,178, 5,474,995, 5,510,368 and WO documents WO96/06840, WO96/03388, WO96/03387, WO96/25405, WO95/15316, WO94/15932, WO94/27980, WO95/00501, WO94/13635, WO94/20480, and WO94/26731.

Drugs such as valdecoxib, celecoxib, and rofecoxib are intended to selectively inhibit COX-2 with minimal effect on COX-1. However, despite the emphasis on COX-2 inhibition, even these drugs appear to have serious long term side effects, such as the breakdown in digestive protective mucus and prevention of normal healing processes. There is thus a continuing need for more specific and non-specific COX-2 inhibitors which avoid side effects associated with COX-1 inhibition.

$LTB_4$. Leukotriene (LT) biosynthesis occurs mainly in granulocytes, monocytes/macrophages and mast cells and an orchestrated interplay between several key enzymes is crucial for efficient formation of leukotrienes, which are proinflammatory mediators released mainly from myeloid cells. 5-Lipoxygenase (5-LO) plays an essential role in the biosynthesis of leukotrienes. As shown in FIG. 1, on cell stimulation elevated $Ca^{2+}$ levels and activated signal transduction cascades activate 5-lipoxygenase (5-LO) and lead to the release of arachidonic acid (AA) from phospholipids by phospholipase $A_2$ ($PLA_2$). AA is metabolized by 5-LO to the unstable intermediate $LTA_4$, that can be converted to $LTB_4$ by $LTA_4$ hydrolase, or conjugated with glutathione to $LTC_4$ by $LTC_4$ synthase, depending on the enzymes present.

The biological actions of LTs are mediated by specific receptors. LTs are potent biological mediators in the pathophysiology of inflammatory diseases and host defense reactions. $LTB_4$ is a potent chemotactic and chemokinetic mediator stimulating the immigration and activation of granulocytes, leading to adherence of granulocytes to vessel walls, degranulation, release of superoxide and lysosomal enzymes, and augments phagocytosis of neutrophils and macrophages. It exerts its effects via binding to the BLT1 and BLT2 receptors. In addition, $LTB_4$ binds and activates the peroxisome proliferator-activated receptor-γ, a transcription factor that mediates anti-inflammatory actions. In lymphocytes, $LTB_4$ stimulates the secretion of IgE, IgG and IgM and the expression of low-affinity receptors for IgE, and has been connected to increased interleukin production, transcription, and neutrophil-dependent hyperalgesia. These properties suggest a significant role for $LTB_4$ in the pathogenesis of inflammatory diseases such as arthritis, psoriasis, inflammatory bowel disease, and asthma.

Natural COX-2 Inhibitors. Several herbs have been found to inhibit the COX-2 enzyme. For example, holy basil has been found to possess significant anti-inflammatory properties and is capable of blocking both the cyclooxygenase and lipoxygenase pathways of arachidonate metabolism. Ursolic acid and oleanolic acid, two of the recognized phytonutrients of holy basil, have been found to have a significant COX-2 inhibitory effect.

Similarly, shogaols and gingerols, pungent components of ginger, have been found to inhibit cyclooxygenase. Eugenol, another active constituent of several medical herbs, has also been found to be a 5-lipoxygenase inhibitor and to possess potent anti-inflammatory and/or anti-rheumatic properties.

*Scutellaria baicalensis* also has been found to inhibit the COX-2 enzyme. According to the USDA database, green tea contains six constituents having cyclooxygenase-inhibitor activity. According to the Napralert database, green tea contains fifty one constituents having anti-inflammatory activity. The polyphenols in green tea were found to cause a marked reduction in COX-2. Flavan-3-ol derivatives (+)-catechin, also present in green tea, have been reported to be COX-1 and COX-2 inhibitors. In addition, salicylic acid, another constituent of green tea, also has been found to be a COX-2 inhibitor.

Berberine, found in barberry and Chinese goldthread, has also been found to inhibit COX-2 without inhibiting COX-1 activity.

In U.S. Pat. No. 6,387,416, Applicants disclosed the inventive compositions and their use for reducing inflammation.

The contents of U.S. Pat. No. 6,387,416 are hereby incorporated by reference in their entirety. Surprisingly, as discussed in greater detail below, it has been determined that the inventive compositions are useful for treating oral cancers as well.

Use of COX-2 Inhibitors for Treating Cancer. It has been postulated that COX-2 inhibitors may be useful for treating cancer. Yet only a very few patents actually disclose the use of COX-2 inhibitors for treating any cancers. In U.S. Pat. No. 5,466,823 to Talley, et al., (Pyrazol-1-yl)benzene sulfonamides are disclosed as inhibitors of cyclooxygenase-2, and for use in the treatment of inflammation, arthritis, and pain, and as being useful for preventing colon cancer. However, their use for actually treating colon cancer or for treating or preventing other neoplasias is not disclosed.

U.S. Pat. No. 6,469,040 to Seibert, et al., discloses a method of using a specific, disclosed class of cyclooxygenase-2 inhibitor derivatives in preventing and treating epithelial cell neoplasia in a subject.

U.S. Pat. No. 6,534,540 to Kindness, et al., discloses a combination of the proprietary HMG-CoA reductase inhibitor lovastatin and the proprietary COX-2 inhibitor rofecoxib for the treatment of cancer, especially oral cancers, and a method of treatment of cancer, especially oral cancers, by administering that combination.

Table 1 depicts data on the inhibitory effects of administration of Zileuton and Celecoxib on the incidence of squamous cell carcinoma on DMBA-induced oral carcinogenesis and the levels of LTB4 and PGE2 in the hamster cheek pouch model.

Based on the limited body of art suggesting the use of COX-2 inhibitors for treating any cancer, and the need for effective treatments for oral cancers in particular, it is apparent that there is a great and immediate need for new compositions for treating oral cancers. This need is met by the inventive methods and compositions, which treat oral cancers without significant side effects.

SUMMARY OF THE INVENTIVE SUBJECT MATTER

The present inventive subject matter relates to a method for treating oral cancers in a subject in need thereof, comprising the step of administering an effective amount of a composition to said subject to treat or prevent said oral cancers, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

The present inventive subject matter further relates to a method for treating oral cancers in a subject in need thereof, comprising the step of administering an effective amount of a composition to said subject to treat said tumor, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

In addition, the present inventive subject matter is drawn to a method for treating side effects associated with oral cancers in a subject in need thereof, comprising the step of administering an effective amount of a composition to said subject to treat said side effects, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

TABLE 1

| | | | Visible tumors | | | |
|---|---|---|---|---|---|---|
| Group | Treatment | n | % (n) | Volume (mm$^3$) | Papilloma, % (n) | SCC, % (n) |
| A | Negative control | 15 | — | — | — | — |
| B | Positive control | 26 | 84.6 (2.96 ± 2.12) | 89.2 ± 76.2 | 53.8 (0.96 ± 1.02) | 76.9 (1.68 ± 1.43) |
| C | 3% Zileuton | 24 | 58.3 (1.08 ± 1.4)‡ | 39.9 ± 48.0† | 37.5 (0.56 ± 0.66) | 45.8‡ (0.56 ± 0.66)* |
| D | 6% Zileuton | 28 | 4.64 (0.68 ± 1.20)* | 22.9 ± 31.4† | 32.1 (0.41 ± 0.58)‡ | 32.1† (0.45 ± 0.72)† |
| E | 3% Celecoxib | 26 | 61.5 (1.25 ± 1.41) | 42.2 ± 41.2† | 69.2 (0.68 ± 0.47)‡ | 57.6 (0.88 ± 0.88)‡ |
| F | 6% Celecoxib | 24 | 54.2‡ (1.04 ± 0.70)‡ | 33.3 ± 32.5† | 29.2 (0.31 ± 0.47)* | 50.0† (0.72 ± 0.76)* |
| G | 3% Zileuton + 3% Celecoxib | 25 | 44.0 (0.86 ± 0.70)* | 21.4 ± 31.5† | 48.0 (0.52 ± 0.58) | 36.0* (0.44 ± 0.65)† |

All P values were based on comparison with group B$\chi^2$. test was used for analysis of the incidence of lesions. ANOVA test was used for analysis of the number of lesions. Wilcoxon signed rank test was used for analysis of the tumor volume. Fifteen samples from each group were analyzed for LTB4 and PGE2. All P values were based on comparison with group B with Student's t test.
*P < 0.01.
†P < 0.001.
‡P < 0.05.

Further, the present inventive subject matter relates to methods for modulating protein expression of $LTB_4$ in a target cell, comprising administration of an effective amount of a composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

BRIEF DESCRIPTION OF THE DRAWINGS

FIG. 4 is a series of photographs which depicts DMBA-induced oral lesions of hamster cheek pouch after a three week treatment with DMBA, indicating the development of hyperplasia and dysplasia in these tissues in the hamster cheek pouch carcinogenesis model.

FIG. 5 is a series of photographs which depicts that the inventive compositions inhibit the proliferation of DMBA-induced epithelial cell proliferation, as determined by 5-bromo-2-deoxyuridine (BrdU) uptake and labeling, in the hamster cheek pouch carcinogenesis model.

DETAILED DESCRIPTION OF THE INVENTIVE SUBJECT MATTER

Definitions

Figure 1:
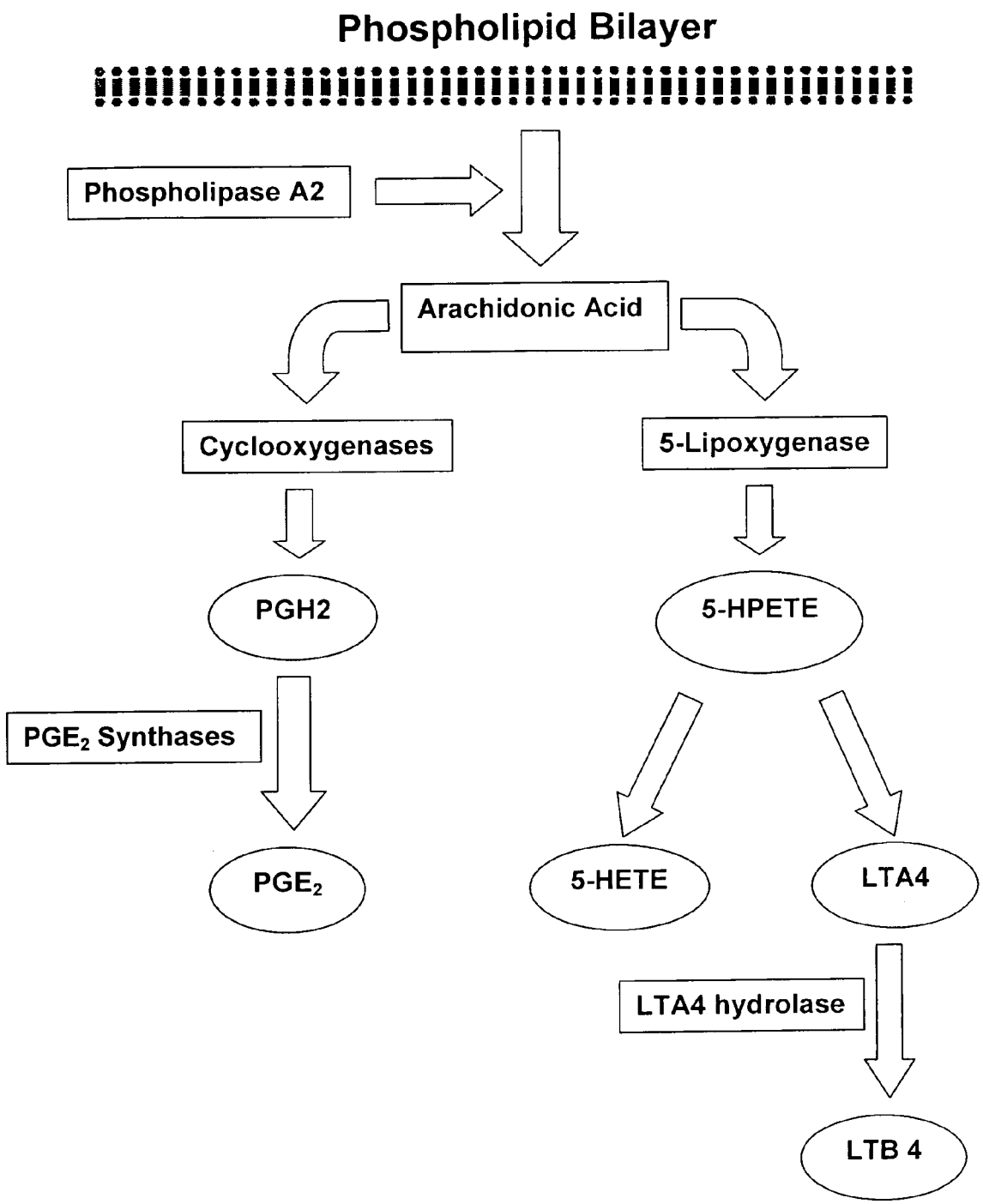
FIG. 1 is a graphic which depicts a schematic representation of the arachidonic acid metabolic pathway involved in oral cancer.
Figure 2A:
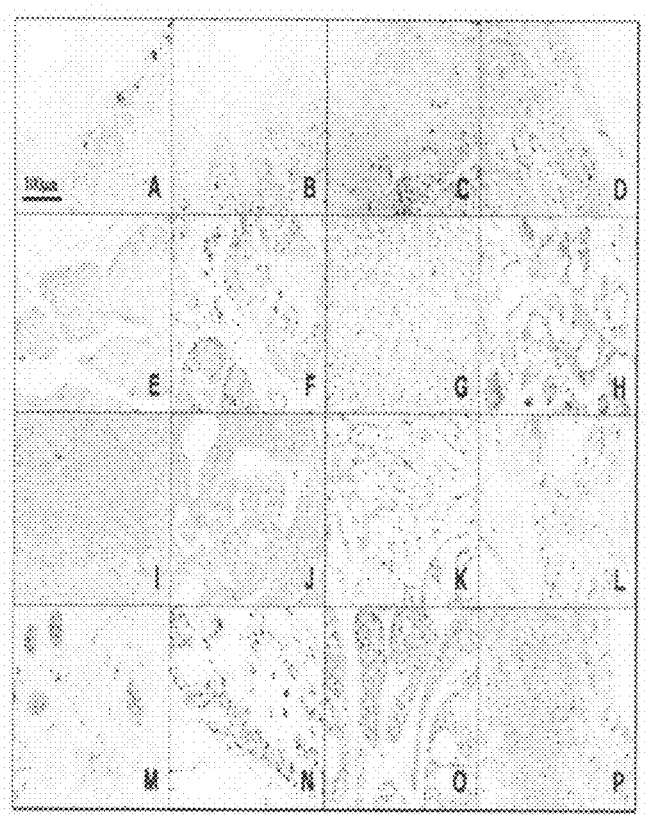
FIG. 2A is a series of immunohistochemistry photographs which depicts the overexpression of 5-LOX in human oral cancer.
Figure 2B:
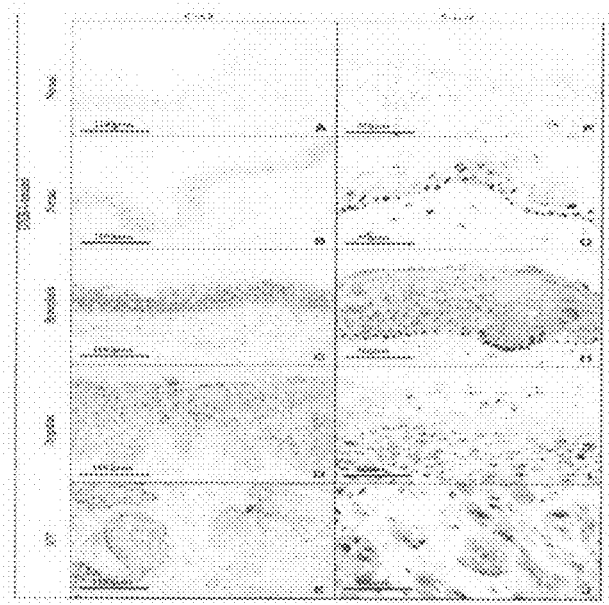
FIG. 2B is a series of immunohistochemistry photographs which depicts the overexpression in hamster oral mucosa of 5-LOX (photographs A-E) and COX-2 (photographs F-J) enzymes.

The term "$LTB_4$" as used herein refers to leukotriene $B_4$.

The term "oral cancers" as used herein refers broadly to neuroglia cell tumors and other malignant tumors or neoplasia of the oral cavity. Oral cancers as used herein refers to cancer that forms in tissues of the lip or mouth, including the front two thirds of the tongue, the upper and lower gums, the lining inside the cheeks and lips, the bottom of the mouth under the tongue, the bony top of the mouth, and the small area behind the wisdom teeth.

The term "therapeutically effective amount" as used herein refers to that amount of the extract which will contribute to the cancer-treating ability of the composition.

The term "treating" as used herein refers to partial or total inhibition of the growth, spreading, or metastasis of oral cancers, as well as partial or total destruction of the cancer cells. The term "treating" includes the reduction or elimination of oral cancers, and also the reduction in the incidence of the disease.

The term "preventing" as used herein refers to either preventing the onset of oral cancers, or preventing the onset of a preclinically evident stage of oral cancers in individuals at risk. Also intended to be encompassed by this definition is the prevention of initiation for malignant cells, and the arrest or reversal of the progression of premalignant cells to malignant cells. "Preventing" also includes the prevention of growth or spreading of the oral cancers. This includes prophylactic treatment of those at risk of developing an oral cancer.

The term "supercritical gas" or "supercritical fluid" as used herein refers to a gas is that heated to a temperature critical point, over which the gas will maintain its gaseous state and not turn to a liquid regardless of pressure. A gas heated to a temperature above its critical point will become very dense on compression, so that its characteristics resemble those of a fluid, but will not become liquid. Carbon dioxide is commonly used in applications requiring a supercritical fluid. The general properties of supercritical fluids and the general use of supercritical fluids in extraction processes are described in, e.g. Taylor, *Supercritical Fluid Extraction*, Wiley, 1996; McHugh and Krukonis, *Supercritical Fluid Extraction: Principles and Practice*, 2nd ed., Butterworth-Heinemann, 1994; and Williams and Clifford, *Supercritical Fluid Methods and Protocols*, Humana Press, 2000, the contents of which are incorporated by reference herein.

The term "supercritical extraction" as used herein refers to the technique in which hydrophobic compounds can be extracted from samples utilizing a supercritical fluid. The salvation power of a supercritical fluid is increased as the pressure and temperature are increased above their critical points, producing an effective solvent for the isolation of hydrophobic molecules.

The term "hydroalcoholic extraction" as used herein refers to the technique in which hydrophilic compounds can be extracted from a sample utilizing a solution of alcohol and water, followed by evaporation of the solution to produce a extract consisting of dissolved solids.

The term "neoplasia" as used herein refers broadly to neoplastic, pre-malignant, and proliferative disease, including specifically benign, premalignant, or malignant neoplasms in individuals with or without any prior history or diagnosis of neoplastic, pre-malignant, or proliferative disease. The term "neoplasia" includes neoplasia that produce prostaglandins or express a cyclooxygenase, including both benign and cancerous tumors, growths, and polyps.

The term "subject" as used herein refers to any human or mammal subject who has an oral cancer, preferably a human subject. For methods of prevention, the subject is any human or animal subject, preferably a human subject, who is at risk for developing an oral cancer. The subject may be at risk due to exposure to carcinogenic agents, being genetically predisposed to have an oral cancer, and the like.

The term "cyclooxygenase-2 inhibitor" or "COX-2 inhibitor" as used herein refers to a compound or composition which is able to inhibit cyclooxygenase-2 without adverse inhibition of cyclooxygenase-1.

The term "RBL-1" as used herein refers to the rat basophilic leukemia-1a cell line, which overproduces the bioactive lipid LTB4.

The Inventive Compositions

The inventive compositions are a genus of polyherbal preparations comprising constituents which exhibit anti-proliferative, anti-inflammatory, antioxidant, anti-angiogenic, and apoptotic activities. The compositions of the present inventive subject matter generally comprise standardized supercritical $CO_2$ concentrated extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

In one aspect, the active composition comprises:

(A) from about 4.5% to about 7.5%, and more preferably from about 5.5% to about 6.5%, by weight of the hydroalcoholic extract of ginger;

(B) from about 5.5% to about 8.5%, and more preferably from about 6% to about 8%, by weight of the supercritical extract of ginger;

(C) from about 1.0% to about 1.5%, and more preferably from about 1.2% to about 1.4%, by weight of the supercritical extract of turmeric;

(D) from about 10.0% to about 16.0%, and more preferably from about 11.5% to about 14.5%, by weight of the supercritical extract of rosemary;

(E) from about 4.0% to about 6.0%, and more preferably from about 4.5% to about 5.5%, by weight of the supercritical extract of oregano;

(F) from about 10.0% to about 16.0%, and more preferably from about 11.5% to about 14.5%, by weight of the hydroalcoholic extract of turmeric;

(G) from about 5.5% to about 8.0%, and more preferably from about 6.0% to about 7.0%, by weight of the hydroalcoholic extract of rosemary;

(H) from about 10.0% to about 16.0%, and more preferably from about 11.5% to about 14.5%, by weight of the hydroalcoholic extract of holy basil;

(I) from about 10.0% to about 16.0%, and more preferably from about 11.5% to about 14.5%, by weight of the hydroalcoholic extract of green tea;

(J) from about 8.0% to about 12.0%, and more preferably from about 9.0% to about 11.0%, by weight of the hydroalcoholic extract of huzhang;

(K) from about 4.0% to about 6.0%, and more preferably from about 4.5% to about 5.5%, by weight of the hydroalcoholic extract of Chinese goldthread;

(L) from about 4.0% to about 6.0%, and more preferably from about 4.5% to about 5.5%, by weight of the hydroalcoholic extract of barberry; and (M) from about 2.0% to about 3.0%, and more preferably from about 2.25% to about 2.75%, by weight of the hydroalcoholic extract of *Scutellaria baicalensis*.

Optionally, the hydroalcoholic extract of ginger, rosemary, turmeric, or oregano used in the present invention is preferably prepared as follows. The plant or a part thereof, which is preferably cryogenically ground to preserve heat sensitive components, is subjected to supercritical extraction, preferably with carbon dioxide, to obtain an oil extract, referred to herein as "the supercritical extract". In an additional optional embodiment, an oil-free residue is isolated from the first step and is then extracted in a water/alcohol, preferably water/ethanol, mixture composed of 60-80 parts alcohol and 40-20 parts water. The alcohol/water liquid is then evaporated off, leaving a powdered extract residue, referred to herein as "the hydroalcoholic extract".

Supercritical extracts of ginger, rosemary, turmeric and oregano optionally used in the present invention can be prepared according to known supercritical extraction methods, such as disclosed, e.g., in E. Stahl, K. W. Quirin, D. Gerard, Dense Gases for Extraction and Refining, Springer Verlag 4 1988, which is hereby incorporated by reference herein.

In a preferred aspect, the weight ratio of the supercritical extract of ginger to the hydroalcoholic extract of ginger is from about 0.8:1 to about 1.4:1.

The hydroalcoholic extracts of rosemary, turmeric, holy basil, green tea, huzhang, Chinese goldthread, barberry and *Scutellaria baicalensis* used in the present invention can be prepared according to conventional hydroalcoholic extraction techniques. For example, the hydroalcoholic extracts can be prepared by extracting the plant portion in a water/alcohol, preferably water/ethanol, mixture preferably composed of 60-80 parts alcohol and 40-20 parts water, and then evaporating off the water/alcohol liquid, leaving a powdered extract residue referred to herein as "the hydroalcoholic extract".

In yet another aspect, the weight ratio of the hydroalcoholic extract of turmeric to the supercritical extract of turmeric is from about 8:1 to about 12:1.

In an alternate aspect, the weight ratio of the supercritical extract of rosemary to the hydroalcoholic extract of rosemary is from about 1.6:1 to about 2.4:1.

In a still further aspect, the hydroalcoholic extract of ginger comprises from about 2.4% to about 3.6%, more preferably from about 2.7% to about 3.3%, and most preferably about 3.0%, by weight of pungent compounds.

In another aspect, the supercritical extract of ginger comprises from about 24% to about 36%, more preferably from about 27% to about 33%, and most preferably about 30%, by weight of pungent compounds; and from about 6.4% to about 9.6%, more preferably from about 7.2% to about 8.8%, and most preferably about 8%, by weight of zingiberene.

In a further aspect, the supercritical extract of turmeric comprises from about 36% to about 54%, more preferably from about 40.5% to about 49.5%, and most preferably about 45%, by weight of turmerones.

In another aspect, the supercritical extract of rosemary comprises from about 18.4% to about 27.6%, more preferably from about 20.7% to about 25.3%, and most preferably about 23%, by weight of total phenolic antioxidants.

In yet another aspect, the supercritical extract of oregano comprises greater than about 4.0%, more preferably from about 4.5% to about 5.5%, and most preferably about 5.0%, by weight of total phenolic antioxidants.

In a still further aspect, the hydroalcoholic extract of turmeric comprises from about 5.6% to about 8.4%, more preferably from about 6.3% to about 7.7%, and most preferably about 7%, by weight of curcumin.

In another aspect, the hydroalcoholic extract of rosemary comprises from about 18.4% to about 27.6%, more preferably from about 20.7% to about 25.3%, and most preferably about 23%, by weight of total phenolic antioxidants.

In a further embodiment, the hydroalcoholic extract of holy basil comprises from about 1.6% to about 2.4%, more preferably from about 1.8% to about 2.2%, and most preferably about 2%, by weight of ursolic acid.

In a further aspect, the hydroalcoholic extract of green tea comprises from about 36% to about 54%, more preferably from about 40.5% to about 49.5%, and most preferably about 45%, by weight of polyphenols.

In another aspect, the hydroalcoholic extract of huzhang comprises from about 6.4% to about 9.6%, more preferably from about 7.2% to about 8.8%, and most preferably about 8%, by weight of resveratrol.

In another embodiment, the hydroalcoholic extract of Chinese goldthread comprises from about 4.8% to about 7.2%, more preferably from about 5.4% to about 6.6%, and most preferably about 6%, by weight of berberine.

In a further aspect, the hydroalcoholic extract of barberry comprises from about 4.8% to about 7.2%, more preferably from about 5.4% to about 6.6%, and most preferably about 6%, by weight of berberine.

In an alternate aspect, said composition comprises:

(A) from about 4.5% to about 7.5% by weight of the hydroalcoholic extract of ginger, wherein the extract comprises from about 2.4% to about 3.6% by weight of pungent compounds;

(B) from about 5.5% to about 8.5% by weight of the supercritical extract of ginger, wherein the extract comprises from about 24% to about 36% by weight of pungent compounds and from about 6.4% to about 9.6% by weight of zingiberene;

(C) from about 1.0% to about 1.5% by weight of the supercritical extract of turmeric, wherein the extract comprises from about 36% to about 54% by weight of turmerones;

(D) from about 10.0% to about 16.0% by weight of the supercritical extract of rosemary, wherein the extract comprises from about 18.4% to about 27.6% by weight of total phenolic antioxidants;

(E) from about 4.0% to about 6.0% by weight of the supercritical extract of oregano, wherein the extract comprises greater than about 4.0% by weight of total phenolic antioxidants;

(F) from about 10.0% to about 16.0% by weight of the hydroalcoholic extract of turmeric, wherein the extract comprises from about 5.6% to about 8.4% by weight of curcumin;

(G) from about 5.5% to about 8.0% by weight of the hydroalcoholic extract of rosemary, wherein the extract comprises from about 18.4% to about 27.6% by weight of total phenolic antioxidants;

(H) from about 10.0% to about 16.0% by weight of the hydroalcoholic extract of holy basil, wherein the extract comprises from about 1.6% to about 2.4% by weight of ursolic acid;

(I) from about 10.0% to about 16.0% by weight of the hydroalcoholic extract of green tea, wherein the extract comprises from about 36% to about 54% by weight of polyphenols;

(J) from about 8.0% to about 12.0% by weight of the hydroalcoholic extract of huzhang, wherein the extract comprises from about 6.4% to about 9.6% by weight of resveratrol;

(K) from about 4.0% to about 6.0% by weight of the hydroalcoholic extract of Chinese goldthread, wherein the extract from about 4.8% to about 7.2% by weight of berberine;

(L) from about 4.0% to about 6.0% by weight of the hydroalcoholic extract of barberry, wherein the extract from about 4.8% to about 7.2% by weight of berberine; and (M) from about 2.0% to about 3.0% by weight of the hydroalcoholic extract of Scutellaria baicalensis;

and wherein said composition further comprises:

(i) the supercritical extract of ginger and the hydroalcoholic extract of ginger at a weight ratio of from about 0.8 to about 1.4 parts of supercritical extract per 1 part of hydroalcoholic extract;

(ii) the hydroalcoholic extract of turmeric and the supercritical extract of turmeric at a weight ratio of from about 8 to about 12 parts of hydroalcoholic extract per 1 part of supercritical extract; and (iii) the supercritical extract of rosemary and the hydroalcoholic extract of rosemary at a weight ratio of from about 1.6 to about 2.4 parts of supercritical extract per 1 part of hydroalcoholic extract.

In an alternate aspect, the composition comprises an additional agent selected from the group consisting of antineoplastic agents, growth inhibiting agents, and nutrients.

Set forth in Table 1 is a preferred embodiment of the orally administered composition, excluding inactive ingredients, as used in the inventive methods. The amounts recited in Table 2 represent the preferred dosage of the ingredients listed.

TABLE 2

| Herb | Type Of Extract | Plant Part | Amount (mg) |
| --- | --- | --- | --- |
| Rosemary | supercritical | leaf | 100 |
| Rosemary | hydroalcoholic (23% TPA 34.5 mg) | leaf | 50 |
| Turmeric | supercritical (45% turmerones 4.5 mg) | rhizome | 10 |
| Turmeric | hydroalcoholic (7% curcumin 7 mg) | rhizome | 100 |
| Ginger | supercritical (30% pungent compounds 16.2 mg 8% zingiberene) | rhizome | 54 |
| Ginger | hydroalcoholic (3% pungent compounds) | rhizome | 46 |
| Holy basil | hydroalcoholic (2% ursolic acid 2 mg) | leaf | 100 |
| Green tea | hydroalcoholic (45% polyphenols 45 mg) | leaf | 100 |
| Huzhang | hydroalcoholic (8% resveratrol 6.4 mg) | root & rhizome | 80 |
| Chinese Goldthread | hydroalcoholic (6% berberine) | root | 40 |
| Barberry | hydroalcoholic (6% berberine 2.4 mg) | root | 40 |
| Oregano | supercritical (≧4.0% TPA 1.8 mg) | leaf | 40 |
| Scutellaria Baicalensis | hydroalcoholic (5:1) | root | 20 |

Preferably, the composition set forth in Table 2 also includes extra virgin olive oil and yellow beeswax.

Methods for Treating Oral Cancers

Diet is considered as one of the most important modifiable factors in coronary heart disease and carcinogenesis. Recent evidence indicates that modulation of inflammation by compounds found in many herbs and spices may be one of the mechanisms by which diet influences development and progression of these common chronic conditions.

Both arachidonic acid and its precursor, linoleic acid, are present in significant quantities in animal fats and a variety of vegetable oils. Physiologically, these fatty acids are integral components of cellular membranes and also function as substrates for the production of an important group of potent, signaling lipids, termed eicosanoids. Eicosanoids are known to be involved in the initiation of the inflammatory response, fever production, regulation of blood pressure, blood clotting, control of reproductive processes and tissue growth, and regulation of the sleep/wake cycle. Additionally, these powerful mediators and the enzymes that produce them, cyclooxygenases (COX) and lipoxygenases (LO), are implicated in tumor development, progression, and metastasis.

The three main isoforms of cyclooxygenase are COX-1, COX-2, and COX-3, and these enzymes are responsible for the production of the group of eicosanoids, prostaglandins. The COX-1 isoform has many important housekeeping functions in the cell, and is therefore constitutively produced throughout the body. COX-2, however, is usually absent until induced by specific stimuli. It is therefore not surprising that COX-2 is implicated in the progression of many disease states, including cancer. COX-2 has been found to be present in elevated levels in a variety of cancers, including lung, colon, pancreatic, head and neck, and glioblastoma. As discussed above, COX-3 has only been relatively recently identified.

A wide spectrum of human malignancies aberrantly overexpress pro-inflammatory cyclooxygenase-2 (COX-2) and 5-lipoxygenase (5-LO) enzymes and inhibitors of these molecules may be useful in cancer chemoprevention and treatment. For this application, Applicants examined the short- and long-term anti-inflammatory effects of Zyflamend herbal preparation (New Chapter, Inc., Brattleboro, Vt.; hereinafter "the inventive compositions") on the development of precursors of oral cancers such as oral squamous cell carcinoma.

The centuries old natural remedy of using white willow bark (*Salix alba*) to provide some pain relief led to the discovery of aspirin, and eventually, to the elucidation of its mechanism of action as a COX inhibitor. Based on this lead and other traditional Eastern medicinal practices, many researchers have looked to a variety of natural plant extracts and natural products for the discovery of both non-specific COX and specific COX-2 inhibitors. Some herbal extracts and natural products that have peaked interest amongst researchers include curcumin, ginger, holy basil, resveratrol, thundergod vine, and berberine from barberry and Chinese goldthread.

Applicants have developed a mixture comprised of herbal extracts, and the mixture has COX-2 inhibitory activity. The inventive compositions are unique, in that they are prepared via a supercritical $CO_2$ extraction process. Unlike traditional solvent based extraction methods, supercritical $CO_2$ extraction allows the natural products in the herbs to be obtained without leaving chemical residues behind in the preparation.

Surprisingly, in addition to the anti-inflammatory action disclosed in U.S. Pat. No. 6,387,416, Applicants have found evidence suggesting that using the inventive compositions inhibits the development and growth of oral cancers. Without being bound by any particular mechanism of action, Applicant expects that chronic inflammation contributes to carcinogenesis in oral cancers, and further expects that aberrant arachidonic acid metabolism, especially as relates to COX and 5-LOX activities, is associated with carcinogenesis in the human oral cavity. The inventive subject matter is based on the discovery that a combination of certain herbs properly extracted and blended in appropriate proportions can used in treating oral cancers. Thus, Applicants expect that compositions comprising a therapeutically effective amount of extracts of one or more of rosemary, turmeric, oregano, ginger, holy basil, ginger, turmeric, *Scutellaria baicalensis*, rosemary, green tea, huzhang, Chinese goldthread, or barberry, and combinations thereof, are effective in treating oral cancers.

The data and results presented in Examples 2 and 3 below demonstrate the following significant points:

The early stages of inflammation in oral tissue induced by a carcinogen can be largely inhibited by treatment with the inventive compositions by oral local application.

If left untreated, early inflammatory lesions can lead to squamous cell carcinoma. Treatment of hamsters with the inventive compositions leads to a dose dependent inhibition of oral cancer.

We believe that oral cancer is due at least in part to an overproduction of the bioactive lipid leukotriene B4, which appears to be a potent proinflammatory eicosanoid in this particular disease.

Applicants have found that hamster oral tissue is elevated in LTB4 after application of the carcinogen DMBA. Administration of the inventive compositions leads to a significant reduction in LTB4 in this tissue.

Using the RBL-1 cell line, which overproduces LTB4, we have shown that the inventive compositions are very effective at inhibiting production of this eicosanoid. This inhibition is correlated with inhibition of proliferation of RBL-1 cells.

Applicants have shown that adding LTB4 back to RBL-1 cells can reverse the growth inhibition of the inventive compositions against RBL-1 cells. Applicants expect that this demonstrates that growth inhibition of RBL-1 cells mediated by the inventive compositions is in fact related to the specific inhibition of LTB4.

Because oral cancer overproduces LTB4, which drives inflammation and subsequent cancer and the inventive compositions inhibit carcinogen-mediated inflammation in oral tissues and does so through an inhibition of formation of LTB4, Applicants expect that the inventive compositions are a very effective inhibitor of oral tissue progression from inflammation to squamous cell cancer in the hamster cheek model. Applicants further expect that this model is predictive of the effect in humans and other animals, and thus the experimental results discussed below lead Applicants to further expect that the inventive compositions are effective against human oral cancer. As there are very few effective treatment options available for control of oral cancer in humans, the inventive compositions therefore are expected to represent a novel and effective treatment option.

Thus, in particular, the present inventive subject matter relates to a method for treating oral cancer in a subject in need thereof, comprising the step of administering an effective amount of a preferred composition to said subject to treat or prevent said oral cancer, wherein the composition comprises therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

In one aspect, said composition is administered orally.

In another preferred embodiment, the orally administered composition is in the form of one or more capsules, one or more tablets, or one or more pills.

In another aspect, the composition comprises:

(A) from about 4.5% to about 7.5%, and more preferably from about 5.5% to about 6.5%, by weight of the hydroalcoholic extract of ginger;

(B) from about 5.5% to about 8.5%, and more preferably from about 6% to about 8%, by weight of the supercritical extract of ginger;

(C) from about 1.0% to about 1.5%, and more preferably from about 1.2% to about 1.4%, by weight of the supercritical extract of turmeric;

(D) from about 10.0% to about 16.0%, and more preferably from about 11.5% to about 14.5%, by weight of the supercritical extract of rosemary;

(E) from about 4.0% to about 6.0%, and more preferably from about 4.5% to about 5.5%, by weight of the supercritical extract of oregano;

(F) from about 10.0% to about 16.0%, and more preferably from about 11.5% to about 14.5%, by weight of the hydroalcoholic extract of turmeric;

(G) from about 5.5% to about 8.0%, and more preferably from about 6.0% to about 7.0%, by weight of the hydroalcoholic extract of rosemary;

(H) from about 10.0% to about 16.0%, and more preferably from about 11.5% to about 14.5%, by weight of the hydroalcoholic extract of holy basil;

(I) from about 10.0% to about 16.0%, and more preferably from about 11.5% to about 14.5%, by weight of the hydroalcoholic extract of green tea;

(J) from about 8.0% to about 12.0%, and more preferably from about 9.0% to about 11.0%, by weight of the hydroalcoholic extract of huzhang;

(K) from about 4.0% to about 6.0%, and more preferably from about 4.5% to about 5.5%, by weight of the hydroalcoholic extract of Chinese goldthread;

(L) from about 4.0% to about 6.0%, and more preferably from about 4.5% to about 5.5%, by weight of the hydroalcoholic extract of barberry; and (M) from about 2.0% to about 3.0%, and more preferably from about 2.25% to about 2.75%, by weight of the hydroalcoholic extract of *Scutellaria baicalensis*.

Optionally, the hydroalcoholic extract of ginger, rosemary, turmeric, or oregano used in the present invention is preferably prepared as follows. The plant or a part thereof, which is preferably cryogenically ground to preserve heat sensitive components, is subjected to supercritical extraction, preferably with carbon dioxide, to obtain an oil extract, referred to herein as "the supercritical extract". In an additional optional embodiment, an oil-free residue is isolated from the first step and is then extracted in a water/alcohol, preferably water/ethanol, mixture composed of 60-80 parts alcohol and 40-20 parts water. The alcohol/water liquid is then evaporated off, leaving a powdered extract residue, referred to herein as "the hydroalcoholic extract".

Supercritical extracts of ginger, rosemary, turmeric and oregano optionally used in the present invention can be prepared according to known supercritical extraction methods, such as disclosed, e.g., in E. Stahl, K. W. Quirin, D. Gerard, Dense Gases for Extraction and Refining, Springer Verlag 4 1988, which is hereby incorporated by reference herein.

In a preferred aspect, the weight ratio of the supercritical extract of ginger to the hydroalcoholic extract of ginger is from about 0.8:1 to about 1.4:1.

The hydroalcoholic extracts of rosemary, turmeric, holy basil, green tea, huzhang, Chinese goldthread, barberry and *Scutellaria baicalensis* used in the present invention can be prepared according to conventional hydroalcoholic extraction techniques. For example, the hydroalcoholic extracts can be prepared by extracting the plant portion in a water/alcohol, preferably water/ethanol, mixture preferably composed of 60-80 parts alcohol and 40-20 parts water, and then evaporating off the water/alcohol liquid, leaving a powdered extract residue referred to herein as "the hydroalcoholic extract".

In yet another aspect, the weight ratio of the hydroalcoholic extract of turmeric to the supercritical extract of turmeric is from about 8:1 to about 12:1.

In an alternate aspect, the weight ratio of the supercritical extract of rosemary to the hydroalcoholic extract of rosemary is from about 1.6:1 to about 2.4:1.

In a still further aspect, the hydroalcoholic extract of ginger comprises from about 2.4% to about 3.6%, more preferably from about 2.7% to about 3.3%, and most preferably about 3.0%, by weight of pungent compounds.

In another aspect, the supercritical extract of ginger comprises from about 24% to about 36%, more preferably from about 27% to about 33%, and most preferably about 30%, by weight of pungent compounds; and from about 6.4% to about 9.6%, more preferably from about 7.2% to about 8.8%, and most preferably about 8%, by weight of zingiberene.

In a further aspect, the supercritical extract of turmeric comprises from about 36% to about 54%, more preferably from about 40.5% to about 49.5%, and most preferably about 45%, by weight of turmerones.

In another aspect, the supercritical extract of rosemary comprises from about 18.4% to about 27.6%, more preferably from about 20.7% to about 25.3%, and most preferably about 23%, by weight of total phenolic antioxidants.

In yet another aspect, the supercritical extract of oregano comprises greater than about 4.0%, more preferably from about 4.5% to about 5.5%, and most preferably about 5.0%, by weight of total phenolic antioxidants.

In a still further aspect, the hydroalcoholic extract of turmeric comprises from about 5.6% to about 8.4%, more preferably from about 6.3% to about 7.7%, and most preferably about 7%, by weight of curcumin.

In another aspect, the hydroalcoholic extract of rosemary comprises from about 18.4% to about 27.6%, more preferably from about 20.7% to about 25.3%, and most preferably about 23%, by weight of total phenolic antioxidants.

In a further embodiment, the hydroalcoholic extract of holy basil comprises from about 1.6% to about 2.4%, more preferably from about 1.8% to about 2.2%, and most preferably about 2%, by weight of ursolic acid.

In a further aspect, the hydroalcoholic extract of green tea comprises from about 36% to about 54%, more preferably from about 40.5% to about 49.5%, and most preferably about 45%, by weight of polyphenols.

In another aspect, the hydroalcoholic extract of huzhang comprises from about 6.4% to about 9.6%, more preferably from about 7.2% to about 8.8%, and most preferably about 8%, by weight of resveratrol.

In another embodiment, the hydroalcoholic extract of Chinese goldthread comprises from about 4.8% to about 7.2%, more preferably from about 5.4% to about 6.6%, and most preferably about 6%, by weight of berberine.

In a further aspect, the hydroalcoholic extract of barberry comprises from about 4.8% to about 7.2%, more preferably from about 5.4% to about 6.6%, and most preferably about 6%, by weight of berberine.

In an alternate aspect, said composition comprises:

(A) from about 4.5% to about 7.5% by weight of the hydroalcoholic extract of ginger, wherein the extract comprises from about 2.4% to about 3.6% by weight of pungent compounds;

(B) from about 5.5% to about 8.5% by weight of the supercritical extract of ginger, wherein the extract comprises from about 24% to about 36% by weight of pungent compounds and from about 6.4% to about 9.6% by weight of zingiberene;

(C) from about 1.0% to about 1.5% by weight of the supercritical extract of turmeric, wherein the extract comprises from about 36% to about 54% by weight of turmerones;

(D) from about 10.0% to about 16.0% by weight of the supercritical extract of rosemary, wherein the extract comprises from about 18.4% to about 27.6% by weight of total phenolic antioxidants;

(E) from about 4.0% to about 6.0% by weight of the supercritical extract of oregano, wherein the extract comprises greater than about 4.0% by weight of total phenolic antioxidants;

(F) from about 10.0% to about 16.0% by weight of the hydroalcoholic extract of turmeric, wherein the extract comprises from about 5.6% to about 8.4% by weight of curcumin;

(G) from about 5.5% to about 8.0% by weight of the hydroalcoholic extract of rosemary, wherein the extract comprises from about 18.4% to about 27.6% by weight of total phenolic antioxidants;

(H) from about 10.0% to about 16.0% by weight of the hydroalcoholic extract of holy basil, wherein the extract comprises from about 1.6% to about 2.4% by weight of ursolic acid;

(I) from about 10.0% to about 16.0% by weight of the hydroalcoholic extract of green tea, wherein the extract comprises from about 36% to about 54% by weight of polyphenols;

(J) from about 8.0% to about 12.0% by weight of the hydroalcoholic extract of huzhang, wherein the extract comprises from about 6.4% to about 9.6% by weight of resveratrol;

(K) from about 4.0% to about 6.0% by weight of the hydroalcoholic extract of Chinese goldthread, wherein the extract from about 4.8% to about 7.2% by weight of berberine;

(L) from about 4.0% to about 6.0% by weight of the hydroalcoholic extract of barberry, wherein the extract from about 4.8% to about 7.2% by weight of berberine; and (M) from about 2.0% to about 3.0% by weight of the hydroalcoholic extract of *Scutellaria baicalensis*;

and wherein said composition further comprises:

(i) the supercritical extract of ginger and the hydroalcoholic extract of ginger at a weight ratio of from about 0.8 to about 1.4 parts of supercritical extract per 1 part of hydroalcoholic extract;

(ii) the hydroalcoholic extract of turmeric and the supercritical extract of turmeric at a weight ratio of from about 8 to about 12 parts of hydroalcoholic extract per 1 part of supercritical extract; and (iii) the supercritical extract of rosemary and the hydroalcoholic extract of rosemary at a weight ratio of from about 1.6 to about 2.4 parts of supercritical extract per 1 part of hydroalcoholic extract.

In a preferred embodiment, the composition is administered in a daily dosage of at least about 700 mg.

In another aspect, the composition is administered on a daily basis for at least 4 weeks.

A still further aspect of the present inventive subject matter is drawn to a method for treating at least one cancerous tumor of the oral cavity in a subject, comprising the step of administering an effective amount of a composition to said subject to treat said tumor, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

In a still further embodiment of the present inventive subject matter, the at least one cancerous tumor is detected during surgery on the oral cavity of said subject, having not been felt by a physician on physical examination of said subject.

Yet still further, the present inventive subject matter includes the at least one cancerous tumor being confined to the oral cavity of said subject and is detected by a physician on physical examination of said subject.

An additional aspect of the present invention includes the cancer related to said at least one cancerous tumor extends beyond the oral cavity of said subject, but has not spread to lymph nodes in said subject.

A further additional aspect of the present inventive subject matter is directed to the cancer related to said at least one cancerous tumor is metastasized to regional lymph nodes or other parts of said subject.

A preferred aspect of the present invention is directed to a method for treating side effects associated with oral cancer in a subject, comprising the step of administering an effective amount of a composition to said subject to treat said side effects, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

In an alternate aspect, the composition comprises an additional agent selected from the group consisting of antineoplastic agents, growth inhibiting agents, and nutrients.

There are large numbers of antineoplastic agents available in commercial use, in clinical evaluation and in pre-clinical development, which optionally are selected for treatment of oral cancers by combination drug chemotherapy. Such antineoplastic agents fall into several major categories: antimetabolite agents, antibiotic-type agents, alkylating agents, hormonal agents, immunological agents, interferon-type agents, metallomatrix proteases, superoxide dismutase mimics or $\alpha_v\beta_3$ inhibitors. Thus, in a preferred embodiment, said antineoplastic agent is selected from the group consisting of antimetabolite agents, antibiotic-type agents, alkylating agents, hormonal agents, immunological agents, interferon-type agents, metallomatrix proteases, superoxide dismutase mimics, and $\alpha_v\beta_3$ inhibitors.

One class of antineoplastic agents which may be used in combination with an inventive composition consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, and uricytin.

A second class of antineoplastic agents which may be used in combination with an inventive composition consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin, and trimelamol.

A third class of antineoplastic agents which may be used in combination with an inventive composition consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, and zorubicin.

A fourth class of antineoplastic agents which may be used in combination with an inventive composition consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, and Yamanouchi YM-534.

Examples of radioprotective agents which may be used in the combination chemotherapy of this invention are AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron), and superoxide dismutase Enzon.

Thus, in a further preferred embodiment, said antineoplastic agent is selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-11, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, and superoxide dismutase.

A benefit provided by the inventive compositions is the utilization of supercritical extraction, an innovative technology for extracting herbs at low temperature without the use of industrial chemical solvents. Such extraction process allows for the highest potency of active compounds in the extracts, as much as 250 times the potency of the original fresh plant material.

The inventive methods use a therapeutically effective amount of the active compositions indicated above. This effective amount will generally comprise from about 0.1 mg to about 100 mg of the active agent per kilogram of patient body weight per day. This effective amount can vary depending upon the physical status of the patient and other factors well known in the art. Moreover, it will be understood that this dosage of active agent can be administered in a single or multiple dosage units to provide the desired therapeutic effect. If desired, other therapeutic agents can be employed in conjunction with those provided by the present inventive subject matter.

The inventive methods use compositions which are preferably delivered to the patient by means of a pharmaceutically acceptable carrier. Such carriers are well known in the art and generally will be in either solid or liquid form. Solid form pharmaceutical preparations which may be prepared according to the present inventive subject matter include powders, tablets, dispersible granules, capsules, and cachets. In general, solid form preparations will comprise from about 5% to about 90% by weight of the active agent.

A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the viscous active compound. In tablets, the active compound is mixed with a carrier having the necessary binding properties in suitable proportions and compacted to the shape and size desired. Suitable solid carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating materials as a carrier which may provide a capsule in which the active component (with or without other carriers) is surrounded by carrier, which is thus in association with it. Similarly, cachets are included. Tablets, powders, cachets, and capsules can be used as solid dosage forms suitable for oral administration. If desired for reasons of convenience or patient acceptance, pharmaceutical tablets prepared according to the inventive subject matter may be provided in chewable form, using techniques well known in the art.

Also contemplated as suitable carriers are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing useful liquid form preparations may be water, isotonic water, ethanol, glycerine, propylene glycol, and the like as well as mixtures thereof. Naturally, the liquid utilized will be chosen with regard to the route of administration. For example, liquid preparations containing large amounts of ethanol are not suitable for parenteral use.

The pharmaceutical preparation may also be in a unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The pharmaceutical preparations of the inventive subject matter may include one or more preservatives well known in the art, such as benzoic acid, sorbic acid, methylparaben, propylparaben and ethylenediaminetetra acetic acid (EDTA). Preservatives are generally present in amounts up to about 1% and preferably from about 0.05 to about 0.5% by weight of the pharmaceutical composition.

Useful buffers for purposes of the inventive subject matter include citric acid-sodium citrate, phosphoric acid-sodium phosphate, and acetic acid-sodium acetate in amounts up to about 1% and preferably from about 0.05 to about 0.5% by weight of the pharmaceutical composition. Useful suspending agents or thickeners include cellulosics like methylcellulose, carageenans like alginic acid and its derivatives, xanthan gums, gelatin, acacia, and microcrystalline cellulose in amounts up to about 20% and preferably from about 1% to about 15% by weight of the pharmaceutical composition.

Sweeteners which may be employed include those sweeteners, both natural and artificial, well known in the art. Sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol, xylitol, mannitol and mixtures thereof may be utilized in amounts from about 10% to about 60% and preferably from about 20% to about 50% by weight of the pharmaceutical composition. Water soluble artificial sweeteners such as saccharin and saccharin salts such as sodium or calcium, cyclamate salts, acesulfame-K, aspartame and the like and mixtures thereof may be utilized in amounts from about 0.001% to about 5% by weight of the composition.

Flavorants which may be employed in the pharmaceutical products of the inventive subject matter include both natural and artificial flavors, and mints such as peppermint, menthol, vanilla, artificial vanilla, chocolate, artificial chocolate, cinnamon, various fruit flavors, both individually and mixed, in amounts from about 0.5% to about 5% by weight of the pharmaceutical composition.

Colorants useful in the present inventive subject matter include pigments which may be incorporated in amounts of up to about 6% by weight of the composition. A preferred pigment, titanium dioxide, may be incorporated in amounts up to about 1%. Also, the colorants may include other dyes suitable for food, drug and cosmetic applications, known as F.D.&C. dyes and the like. Such dyes are generally present in amounts up to about 0.25% and preferably from about 0.05% to about 0.2% by weight of the pharmaceutical composition. A full recitation of all F.D.&C. and D.&C. dyes and their corresponding chemical structures may be found in the Kirk-Othmer Encyclopedia of Chemical Technology, in Volume 5, at pages 857-884, which text is accordingly incorporated herein by reference.

Useful solubilizers include alcohol, propylene glycol, polyethylene glycol and the like and may be used to solubilize the flavors. Solubilizing agents are generally present in amounts up to about 10%; preferably from about 2% to about 5% by weight of the pharmaceutical composition.

Lubricating agents which may be used when desired in the instant compositions include silicone oils or fluids such as substituted and unsubstituted polysiloxanes, e.g., dimethyl polysiloxane, also known as dimethicone. Other well known lubricating agents may be employed.

It is not expected that the inventive methods use compositions which will display significant adverse interactions with other synthetic or naturally occurring substances. Thus, the inventive compositions may be administered in combination with other compounds and compositions useful for treating oral cancers. In particular the inventive methods use compositions which may be administered in combination with other inventive compositions, other antineoplastic substances, and the like.

The optimal pharmaceutical formulations will be determined by one skilled in the art depending upon considerations such as the route of administration and desired dosage. See, for example, "Remington's Pharmaceutical Sciences", 18th ed. (1990, Mack Publishing Co., Easton, Pa. 18042), pp. 1435-1712, which is hereby incorporated by reference in its entirety. Such formulations may influence the physical state, stability, rate of in vivo release, and rate of in vivo clearance of the present therapeutic agents of the inventive subject matter.

Methods for Inhibiting Oral Cancers

The inventive compositions are a combination of ten concentrated herbal extracts and having potent anti-inflammatory activity. The inventive compositions have shown inhibitory activity against COX-1, COX-2, and 5-LOX enzymes, and Applicant has found that the inventive compositions inhibit the development of DMBA-induced inflammation, a precursor of oral squamous cell carcinoma.

Figure 8:
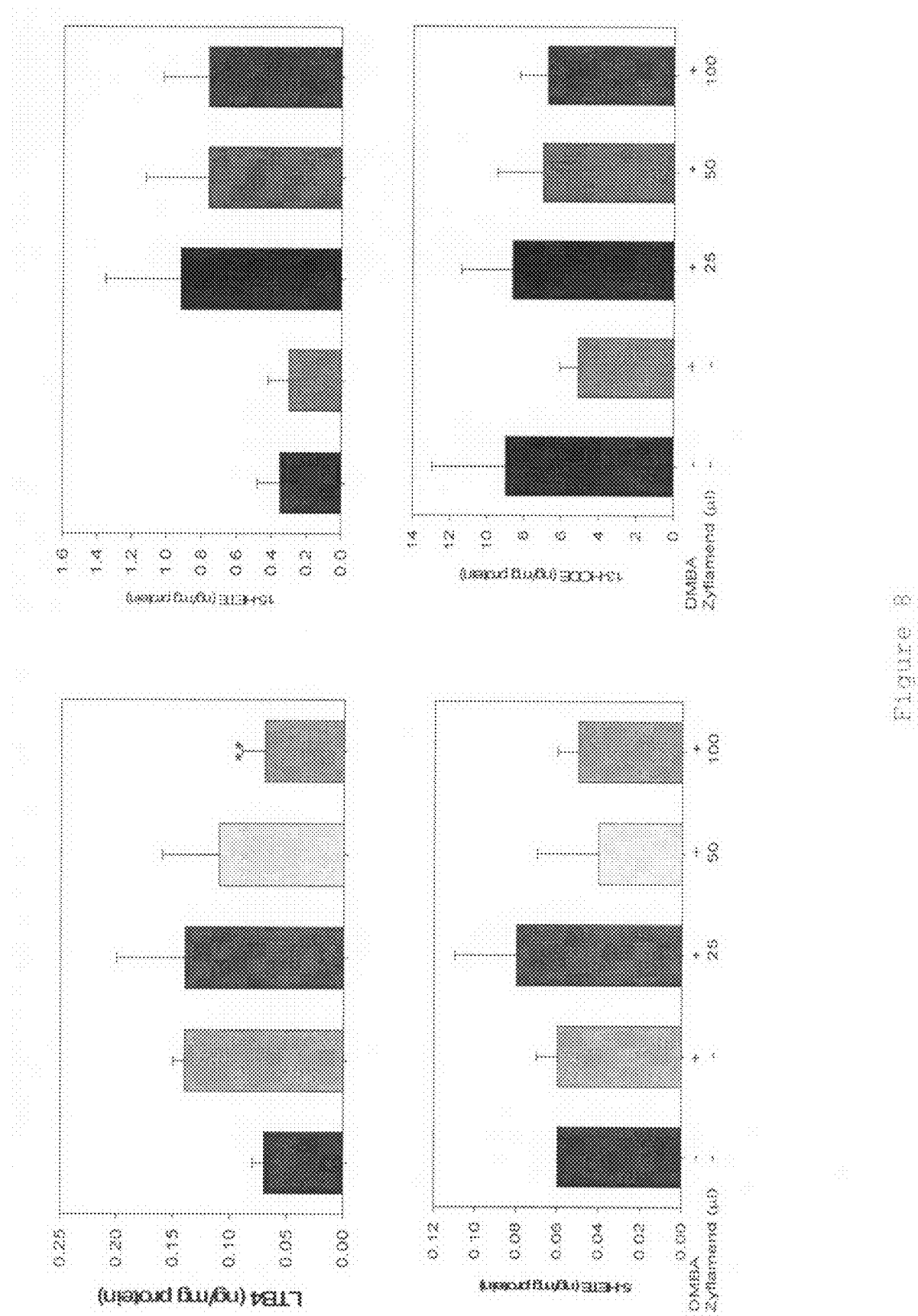
FIG. 8 is a series of bar graphs which depict levels of eicosanoid metabolism in DMBA induced hamster cheek carcinoma treated with the inventive compositions.

Surprisingly, among a number of proteins associated with arachidonic acid metabolism as shown in FIG. 8, the expression of $LTB_4$ alone was significantly increased upon treatment with the inventive compositions.

Without being bound to a particular mechanism of action, the data described herein suggest that one or more compositions which are present in the herbal preparation of the inventive compositions modulate the expression of $LTB_4$ regulate inflammation, and individually or collectively inhibit oral cancer cells. The data suggests that the 5-lipoxygenase pathway is more important than the cyclooxygenase pathway in oral carcinogenesis. Further, these results suggest, and we expect, that the inventive compositions effectively treats and/or prevents oral carcinogenesis at the post-initiation stage, and that its chemopreventive effect relates to its inhibitory effects on $LTB_4$ formation.

Thus, the inventive subject matter further relates to methods for modulating $LTB_4$ expression in a target cell, comprising administration of an effective amount of a composition comprising therapeutically effective amounts of supercritical extracts of rosemary, turmeric, oregano and ginger; and therapeutically effective amounts of hydroalcoholic extracts of holy basil, ginger, turmeric, Scutellaria baicalensis, rosemary, green tea, huzhang, Chinese goldthread, and barberry.

In one aspect of the inventive subject matter, said composition is administered orally.

In another aspect of the inventive subject matter, said orally administered composition is in the form of one or more capsules, one or more tablets, or one or more pills.

In a preferred embodiment, said composition comprises:
(A) from about 4.5% to about 7.5% by weight of the hydroalcoholic extract of ginger;
(B) from about 5.5% to about 8.5% by weight of the supercritical extract of ginger;
(C) from about 1.0% to about 1.5% by weight of the supercritical extract of turmeric;
(D) from about 10.0% to about 16.0% by weight of the supercritical extract of rosemary;
(E) from about 4.0% to about 6.0% by weight of the supercritical extract of oregano;
(F) from about 10.0% to about 16.0% by weight of the hydroalcoholic extract of turmeric;
(G) from about 5.5% to about 8.0% by weight of the hydroalcoholic extract of rosemary;
(H) from about 10.0% to about 16.0% by weight of the hydroalcoholic extract of holy basil;
(I) from about 10.0% to about 16.0% by weight of the hydroalcoholic extract of green tea;
(J) from about 8.0% to about 12.0% by weight of the hydroalcoholic extract of huzhang;
(K) from about 4.0% to about 6.0% by weight of the hydroalcoholic extract of Chinese goldthread;
(L) from about 4.0% to about 6.0% by weight of the hydroalcoholic extract of barberry; and
(M) from about 2.0% to about 3.0% by weight of the hydroalcoholic extract of Scutellaria baicalensis;

and wherein said composition further comprises:
(i) the supercritical extract of ginger and the hydroalcoholic extract of ginger at a weight ratio of from about 0.8 to about 1.4 parts of supercritical extract per 1 part of hydroalcoholic extract;
(ii) the hydroalcoholic extract of turmeric and the supercritical extract of turmeric at a weight ratio of from about 8 to about 12 parts of hydroalcoholic extract per 1 part of supercritical extract; and
(iii) the supercritical extract of rosemary and the hydroalcoholic extract of rosemary at a weight ratio of from about 1.6 to about 2.4 parts of supercritical extract per 1 part of hydroalcoholic extract.

Route(s) of Administration

The compounds and compositions are preferably administered orally in the form of capsules, tablets, aqueous suspensions, or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening, flavoring, coloring agents, or combinations thereof. Delivery in an enterically coated tablet, caplet, or capsule, to further enhance stability and provide release in the intestinal tract to improve absorption, is the best mode of administration currently contemplated.

Dosage

Dosage levels on the order of about 0.001 mg to about 100 mg per kilogram body weight of the active ingredient compounds or compositions are useful in the treatment of the above conditions, with preferred levels ranging from 200 mg per day to 1600 mg per day. The compounds and compositions of the present inventive subject matter may usually be given in two or three doses daily. Starting with a low dose (200-300 mg) twice daily and slowly working up to higher doses if needed is a preferred strategy. The amount of active ingredient that may be combined with the carrier materials to produce a single dosage form will vary depending upon the host treated and the particular mode of administration.

It is to be understood, however, that a specific dose level for any particular patient will depend upon a variety of factors, including the activity of the specific compound employed; the age, body weight, general health, sex and diet of the patient; the time of administration; the rate of excretion; drug combination; the severity of the particular disorder being treated; and the form of administration. One of ordinary skill in the art would appreciate the variability of such factors and would be able to establish specific dose levels using no more than routine experimentation.

EXAMPLES

The following examples are illustrative of the present inventive subject matter and are not intended to be limitations thereon. Unless otherwise indicated, all percentages are based upon 100% by weight of the final composition.

Example 1

Preparation of the Inventive Compositions

The inventive compositions are prepared by methods known in the art, and disclosed in Applicants' U.S. Pat. No. 6,387,416. The preparation of the component elements of the inventive compositions is summarized as follows:

The hydroalcoholic extract of ginger used in the inventive compositions is preferably prepared as follows. The ginger rhizome, which is preferably cryogenically ground to preserve heat sensitive components, is subjected to supercritical extraction to obtain: (i) an oil extract, referred to herein as "the supercritical extract" of ginger, containing delicate lipophilic components, and (ii) an oil-free residue. The oil-free residue is then extracted in a water/alcohol, preferably water/ethanol, mixture composed of 60-80 parts alcohol and 40-20 parts water. The alcohol/water liquid is then evaporated off, leaving a powdered extract residue, referred to herein as "the hydroalcoholic extract" of ginger.

The composition of this invention will preferably contain the supercritical extract and the hydroalcoholic extract of ginger at a weight ratio of preferably from about 0.9 to about 1.4 parts, more preferably from about 1.1 to about 1.3 parts, most preferably about 1.17 parts, of supercritical extract per 1 part post-supercritical hydroalcoholic extract.

The supercritical extracts of ginger, rosemary, turmeric and oregano used in the inventive compositions can be prepared according to known supercritical extraction methods, such as disclosed, e.g., in E. Stahl, K. W. Quirin, D. Gerard, Dense Gases for Extraction and Refining, Springer Verlag 4 1988, which is hereby incorporated by reference herein.

The hydroalcoholic extracts of rosemary, turmeric, holy basil, green tea, huzhang, Chinese goldthread, barberry and *Scutellaria baicalensis* used in the inventive compositions can be prepared according to conventional hydroalcoholic extraction techniques. For example, the hydroalcoholic extracts can be prepared by extracting the plant portion in a water/alcohol (preferably water/ethanol) mixture (preferably composed of 60-80 parts alcohol and 40-20 parts water), and then evaporating off the water/alcohol liquid, leaving a powdered extract residue (referred to herein as "the hydroalcoholic extract").

In the composition of this invention, the hydroalcoholic extract of turmeric and the supercritical extract of turmeric will preferably be present at a weight ratio of preferably from about 8 to about 12 parts, more preferably from about 9 parts to about 11 parts, most preferably about 10 parts, of hydroalcoholic extract per 1 part of supercritical extract.

The composition of this invention will preferably contain the supercritical extract of rosemary and the hydroalcoholic extract of rosemary at a weight ratio of preferably from about 1.6 to about 2.4 parts, more preferably from about 1.8 to about 2.2 parts, most preferably about 2.0 parts, of supercritical extract per 1 part of hydroalcoholic extract.

The hydroalcoholic extract of ginger used in the inventive compositions will preferably contain from about 2.4% to about 3.6%, more preferably from about 2.7% to about 3.3%, most preferably about 3.0%, by weight of pungent compounds (e.g., shogaol).

The supercritical extract of ginger used in the inventive compositions will contain preferably from about 24% to about 36%, more preferably from about 27% to about 33%, most preferably about 30%, by weight of pungent compounds (e.g., shogaol) and preferably from about 6.4% to about 9.6%, more preferably from about 7.2% to about 8.8%, most preferably about 8%, by weight of zingiberene.

The supercritical extract of turmeric used in the inventive compositions will contain preferably from about 36% to about 54%, more preferably from about 40.5% to about 49.5%, most preferably about 45%, by weight of turmerones.

The supercritical extract of rosemary used in the inventive compositions will contain preferably from about 18.4% to about 27.6%, more preferably from about 20.7% to about 25.3%, most preferably about 23%, by weight of total phenolic antioxidants ("TPA").

The supercritical extract of oregano used in the inventive compositions will contain preferably from about 0.64% to about 0.96%, more preferably from about 0.72% to about 0.88%, most preferably about 0.8%, by weight of TPA.

The hydroalcoholic extract of turmeric used in the inventive compositions will contain preferably from about 5.6% to about 8.4%, more preferably from about 6.3% to about 7.7%, most preferably about 7%, by weight of curcumin.

The hydroalcoholic extract of rosemary used in the inventive compositions will contain preferably from about 18.4% to about 27.6%, more preferably from about 20.7% to about 25.3%, most preferably about 23%, by weight of TPA.

The hydroalcoholic extract of holy basil used in the inventive compositions will contain preferably from about 1.6% to about 2.4%, more preferably from about 1.8% to about 2.2%, most preferably about 2%, by weight of ursolic acid.

The hydroalcoholic extract of green tea used in the inventive compositions will contain preferably from about 36% to about 54%, more preferably from about 40.5% to about 49.5%, most preferably about 45%, by weight of polyphonies.

The hydroalcoholic extract of huzhang used in the inventive compositions will contain preferably from about 6.4% to about 9.6%, more preferably from about 7.2% to about 8.8%, most preferably about 8%, by weight of resveratrol.

The hydroalcoholic extract of Chinese goldthread used in the inventive compositions will contain preferably from about 4.8% to about 7.2%, more preferably from about 5.4% to about 6.6%, most preferably about 6%, by weight of berberine.

The hydroalcoholic extract of barberry used in the inventive compositions will contain preferably from about 4.8% to about 7.2%, more preferably from about 5.4% to about 6.6%, most preferably about 6%, by weight of berberine.

Example 2

Short Term Study on the Anti-Inflammatory Effects of the Inventive Composition

DMBA (0.5%, 100 µl) was paint-brushed onto the cheek pouch of test hamsters 3 times per week for three consecutive weeks. Test animals were treated with the inventive compositions at dosages of 25, 50, and 100 µl, administered by topical application a total of three times. Tissue samples were collected six hours after the last treatment with the inventive compositions and subjected to pathological, immunohistochemical, and eicosanoid analysis.

Figure 3A:
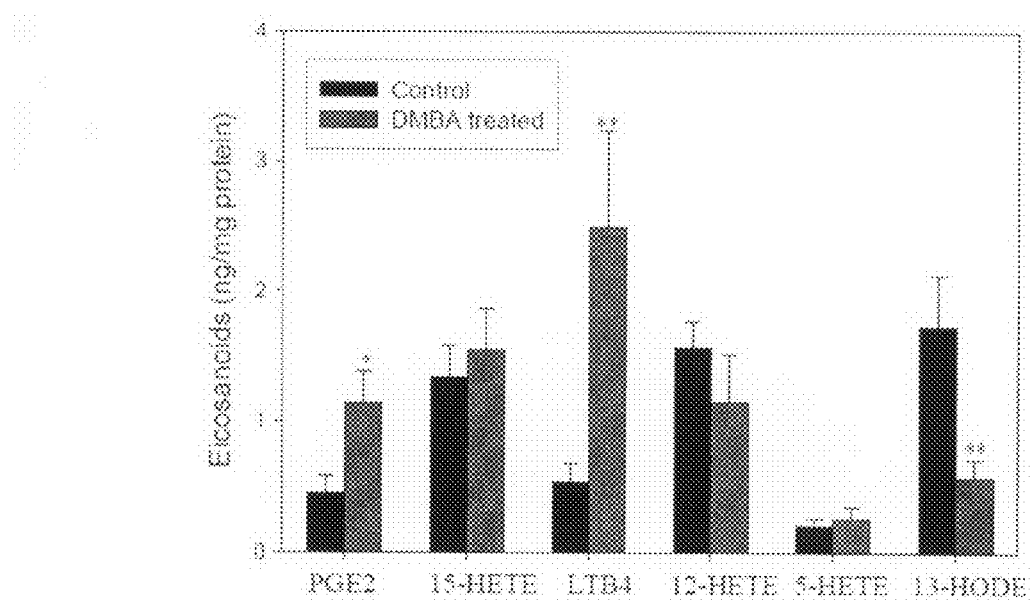
FIG. 3A is a graph which depicts that PGE2 and $LTB_4$ are up-regulated in the DMBA-induced hamster cheek pouch carcinogenesis model used by Applicant.
Figure 3B:
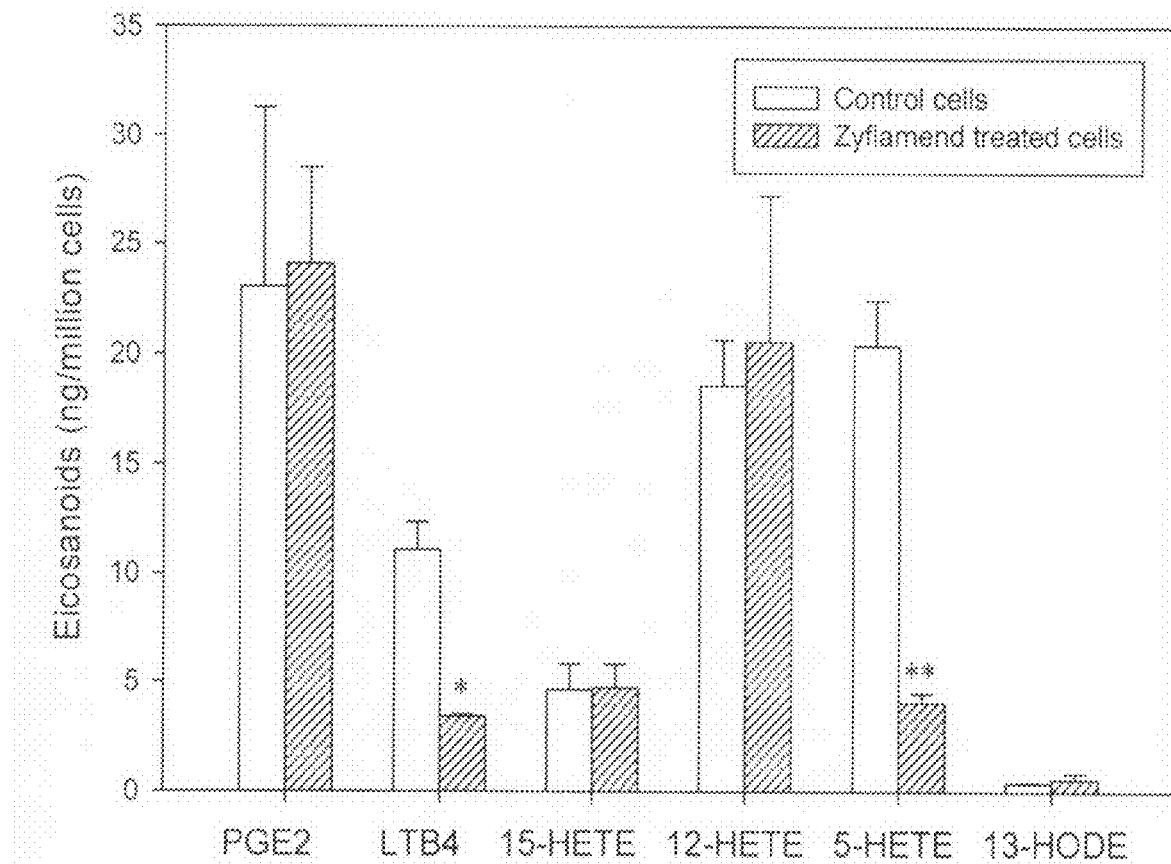
FIG. 3B is a graph which depicts the effect of the inventive compositions on eicosanoid metabolism in RBL-1 cells.

As shown in FIG. 3B, treatment of RBL-1 cells with the inventive compositions resulted in inhibition of formation of LTB4 as well as 5-HETE. These data show that in the RBL-1 cell line, the inventive compositions have a selective effect on bioactive lipid formation. This is of great interest because different malignant diseases have different proinflammatory bioactive lipids that drive their proliferation. Based on our previous work showing that the inventive compositions reduce proliferation of human prostate cells through inhibition of 12-lipoxygenase, the cumulative evidence suggests that the inventive compositions contain unique components that are effective against distinct malignant diseases.

FIG. 4 shows the histopathology of oral lesions of hamster cheek pouch which develop after a three week treatment with DMBA. The photographs show the graded severity of the disease from normal to hyperplasia to dysplasia, as evidenced by HE staining.

Figure 6:
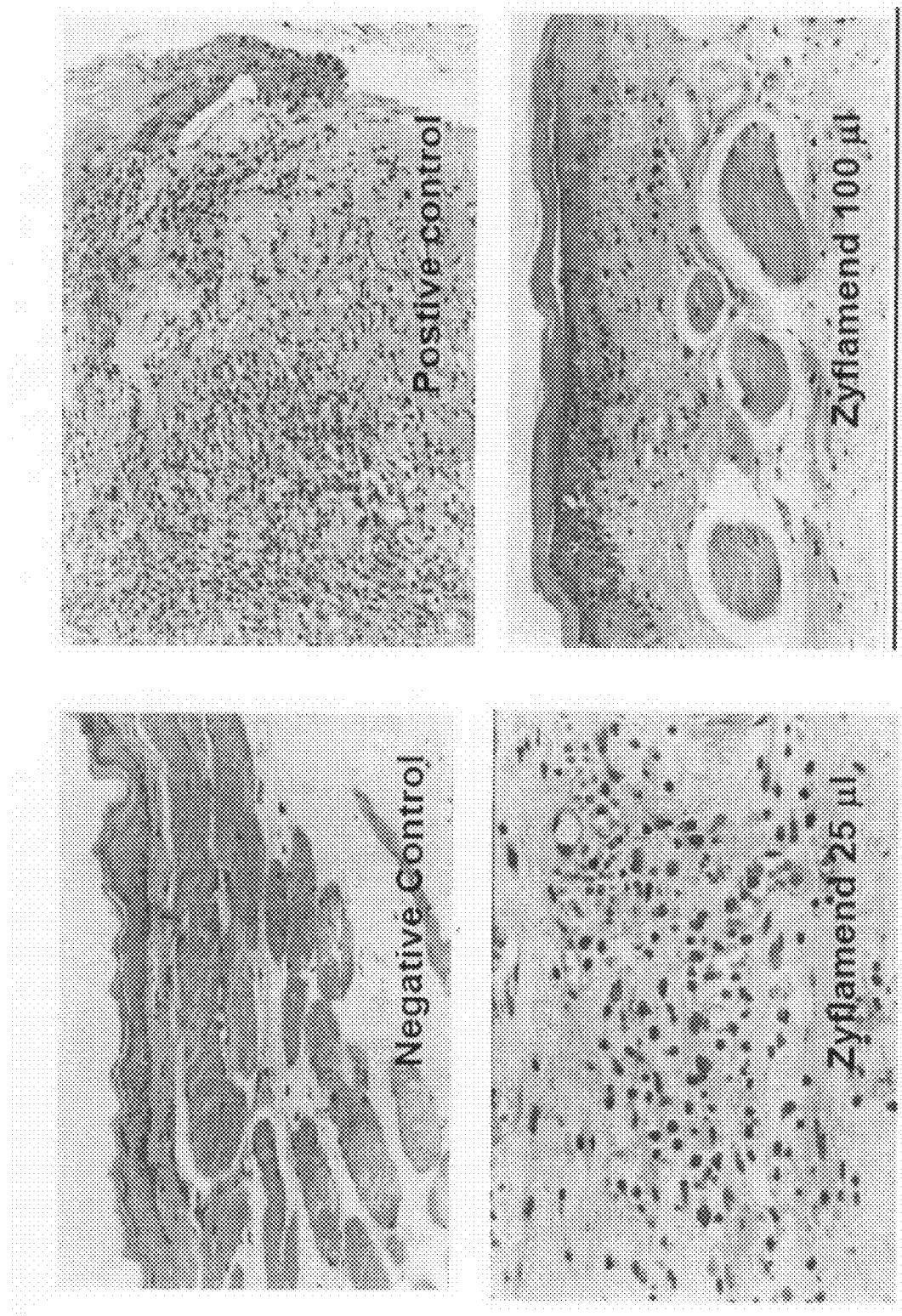
FIG. 6 is a series of photographs which depicts the inhibition of formation of infiltrating inflammatory cells by administration of the inventive composition.

As shown in FIGS. 5 and 6, the inventive compositions significantly inhibited histopathological progression toward the development of hyperplasia and dysplasia, epithelial cell proliferation, and formation of infiltrating inflammatory cells in the DMBA-induced hamster cheek pouch model. The dashed line in FIG. 5 represents a BrdU-labeling index, which is the number of positively stained cells divided by the number of epithelial cells in a defined area. For each case, 4~6 high-power fields (×400) were randomly picked to count more than 1,000 epithelial cells. As shown in FIG. 6, the DMBA induced inflammation was inhibited by the inventive compositions in a concentration dependent manner.

Example 3

Long Term Study on the Anti-Cancer Effects of the Inventive Composition

DMBA (0.5%, 100 µl) was paint-brushed in the cheek pouch of hamsters for 6 weeks, which produces precancerous lesions in positive control animals. Test animals are treated with the inventive compositions at dosages of 25, 50, and 100 µl, the same as that used in the short term study described in Example 1, for a total of 18 weeks. At the end of the experimental period, tissues are collected and examined. These studies confirm Applicant's expectation of anticancer activity of the inventive compositions in the DMBA-induced hamster cheek pouch carcinoma model.

Figure 7:
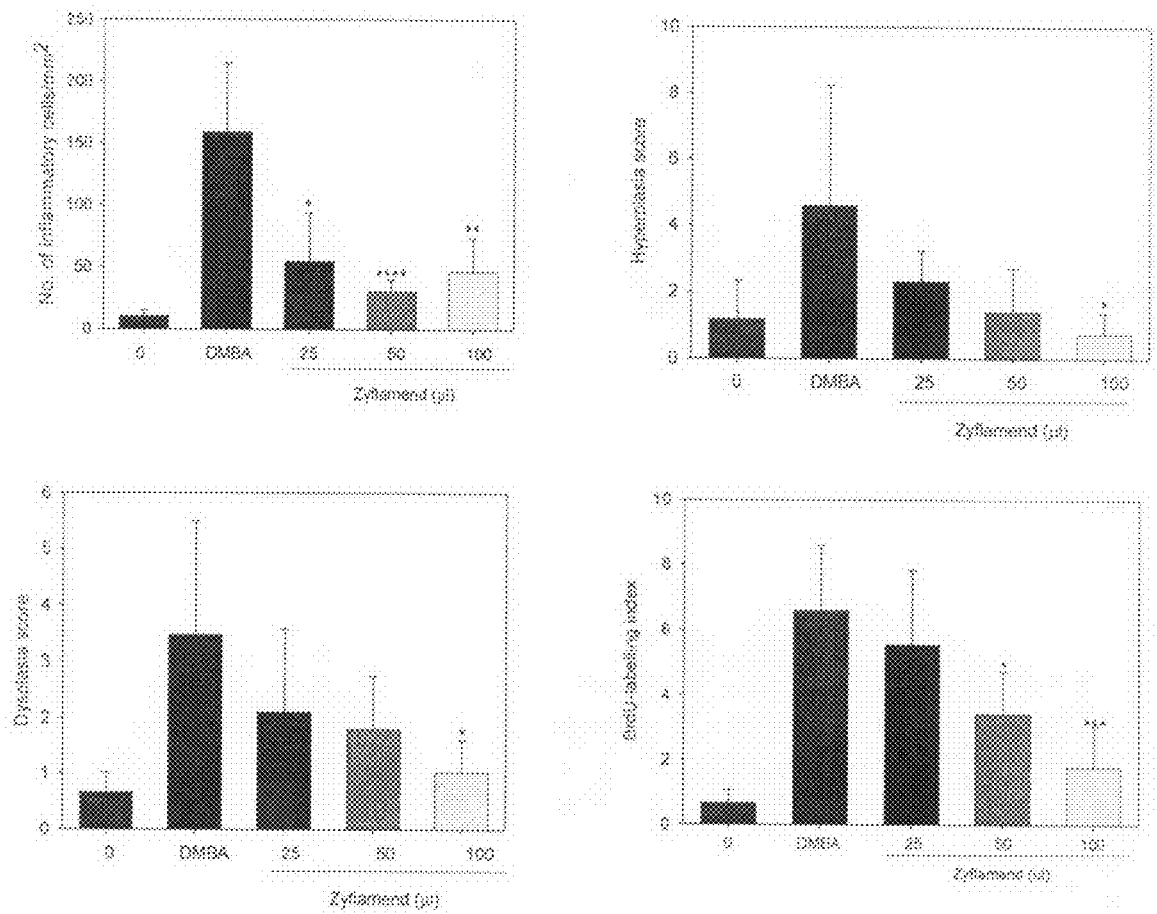
FIG. 7 is a series of bar graphs which depict significantly reduced infiltration of inflammatory cells, incidence of hyperplasia, number of dysplastic lesions, and BrdU labeling index produced in a concentration dependent manner by the administration of the inventive composition.

As shown in FIG. 7, the analysis of hamster cheek pouch tissues exposed to DMBA indicated an increase in proliferation shown in the upper left plot, an increase in hyperplasia shown in the upper right plot, an increase in dysplasia shown in the lower left plot, and an increase in BrdU labeling shown in the lower right plot. Table 3 shows the chemoprotective effects of topical administration of the inventive compositions on DMBA-induced oral carcinogenesis in hamster cheek pouch.

TABLE 3

Chemopreventive effects of topical Zyflamend on DMBA-induced oral carcinogenensis in hamster cheek pouch.

| Group | No. | Treatment | Macroscopic Observation | | |
|---|---|---|---|---|---|
| | | | Incidence % | Number | Volume ($cm^3$) |
| A | 30 | Negative control | 0 | 0 | 0 |
| B | 30 | Positive control | 86.7% (26) | 1.43 ± 1.07 | 5.78 ± 13.57 |
| C | 28 | Zyflamend 50 µl | 53.6% (15)* | 0.93 ± 1.25* | 8.10 ± 33.19 |
| D | 28 | Zyflamend 100 µl | 50.0% (14)* | 0.68 ± 0.86** | 0.45 ± 1.68** |

| Group | Microscopic Observation | | | | |
|---|---|---|---|---|---|
| | Hyperplasia No. | Dysplasia No. (mild & moderate) | Dysplasia No. (severe) | SCC No. | SCC Incidence % |
| A | 0.45 ± 0.37** | 0.10 ± 0.21** | 0 | 0 | 0 |
| B | 3.03 ± 1.64 | 5.17 ± 2.75 | 1.57 ± 1.38 | 2.62 ± 2.00 | 86.7% (26) |
| C | 2.48 ± 1.45 | 3.25 ± 2.46** | 0.96 ± 1.82* | 1.82 ± 1.58 | 71.4% (20) |
| D | 1.59 ± 1.33** | 3.05 ± 1.67** | 0.64 ± 0.64* | 1.59 ± 1.31* | 71.4% (20) |

*$p < 0.05$,
**$p < 0.01$ 5-bromo-2-deoxyuridine uptake may be indicative of new DNA synthesis, and is often associated with cellular proliferation. Treatment of the test hamsters with the inventive compositions, applied to the oral tissue on a daily basis, significantly inhibited all of these parameters of early oral cancer inflammation and premalignant lesions in a dose dependent manner. Table 4 shows the effects of topical administration of the inventive compositions on cell proliferation of DMBA-induced oral carcinogenesis in hamster cheek pouch.

TABLE 4

Effects of topical Zyflamend on cell proliferation (BrdU-labeling index) of DMBA-induced oral carcinogenesis in hamster cheek pouch

| Group | No. | Treatment | Normal | Hyperplasia | Dysplasia | SCC |
|---|---|---|---|---|---|---|
| A | 30 | Negative control | 0.08 ± 0.17** | — | — | — |
| B | 30 | Positive control | 1.93 ± 1.80 | 4.82 ± 3.34 | 9.37 ± 5.98 | 13.01 ± 10.18 |
| C | 28 | Zyflamend 50 µl | 2.43 ± 1.92 | 4.36 ± 3.20 | 8.54 ± 6.02 | 14.72 ± 13.44 |
| D | 28 | Zyflamend 100 µl | 0.77 ± 0.81** | 2.12 ± 1.64** | 5.25 ± 3.73** | 7.35 ± 8.20 |

*p < 0.05,
**p < 0.01

Applicants tested for levels of six eicosanoids, LTB4, 5-HETE, 12-HETE, 15-HETE, 13-HODE, and PGE2, after exposure to DMBA, with and without administration of the inventive compositions. As shown in FIG. 8, among the eicosanoids examined in hamster cheek pouch tissue, the only significant change noted from these analyses was elevation of LTB4 and coordinate inhibition of this elevation by the inventive compositions; levels of LTB4 were reduced by about 50% in hamster cheek pouch tissues treated with 100 µl of the inventive compositions (P<0.05). Data not shown for PGE2 and 12-HETE.

Figure 9:
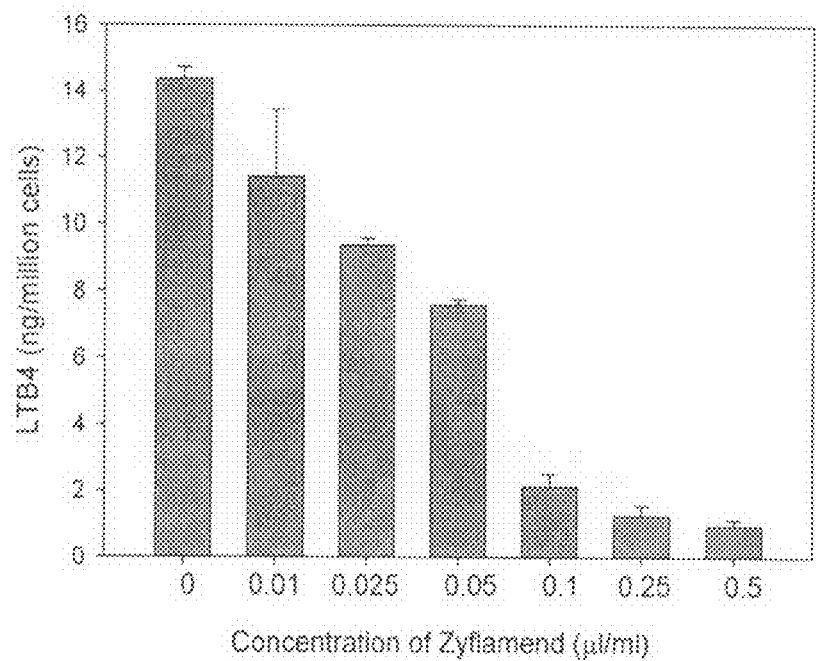
FIG. 9 is a bar graph which depicts inhibition of growth of RBL-1 cells in relation to concentration of the inventive compositions.

As shown in FIG. 9, the inventive compositions inhibited formation of LTB4 in RBL-1 cells and produced a concentration dependent inhibition of growth of RBL-1 cells.

Figure 10:
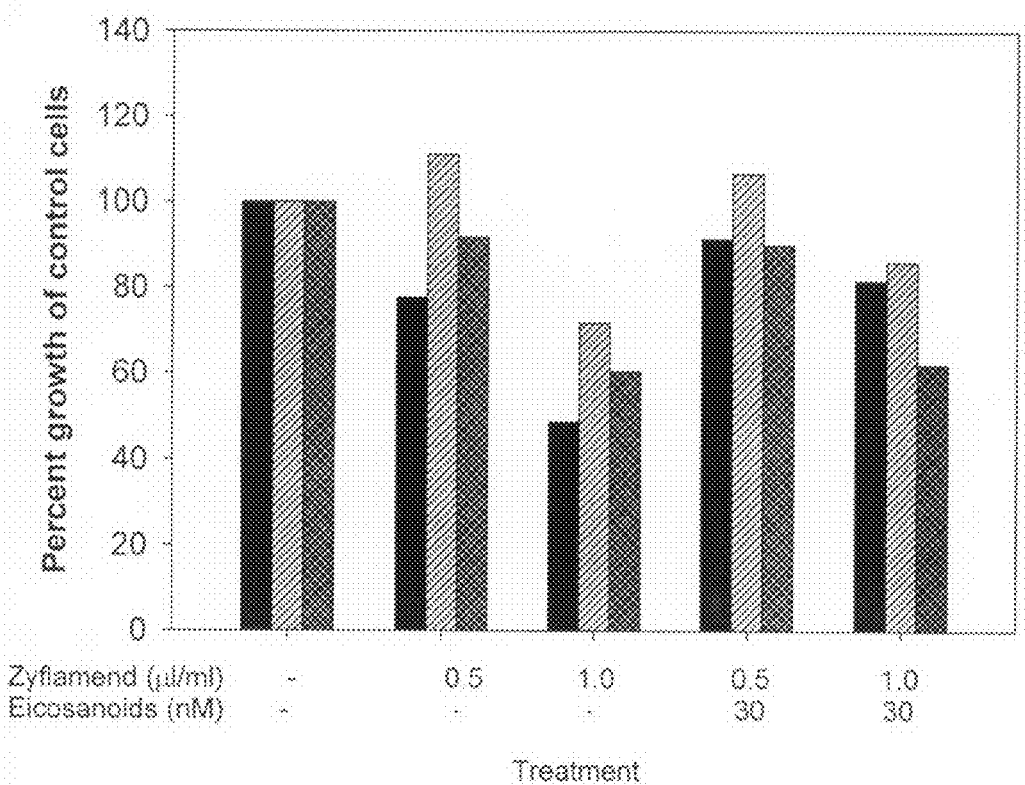
FIG. 10 is a bar graph which depicts data from "add back" experiments of LTB4, PGE2, and 5-HETE in relation to administration of the inventive compositions.
Figure 11:
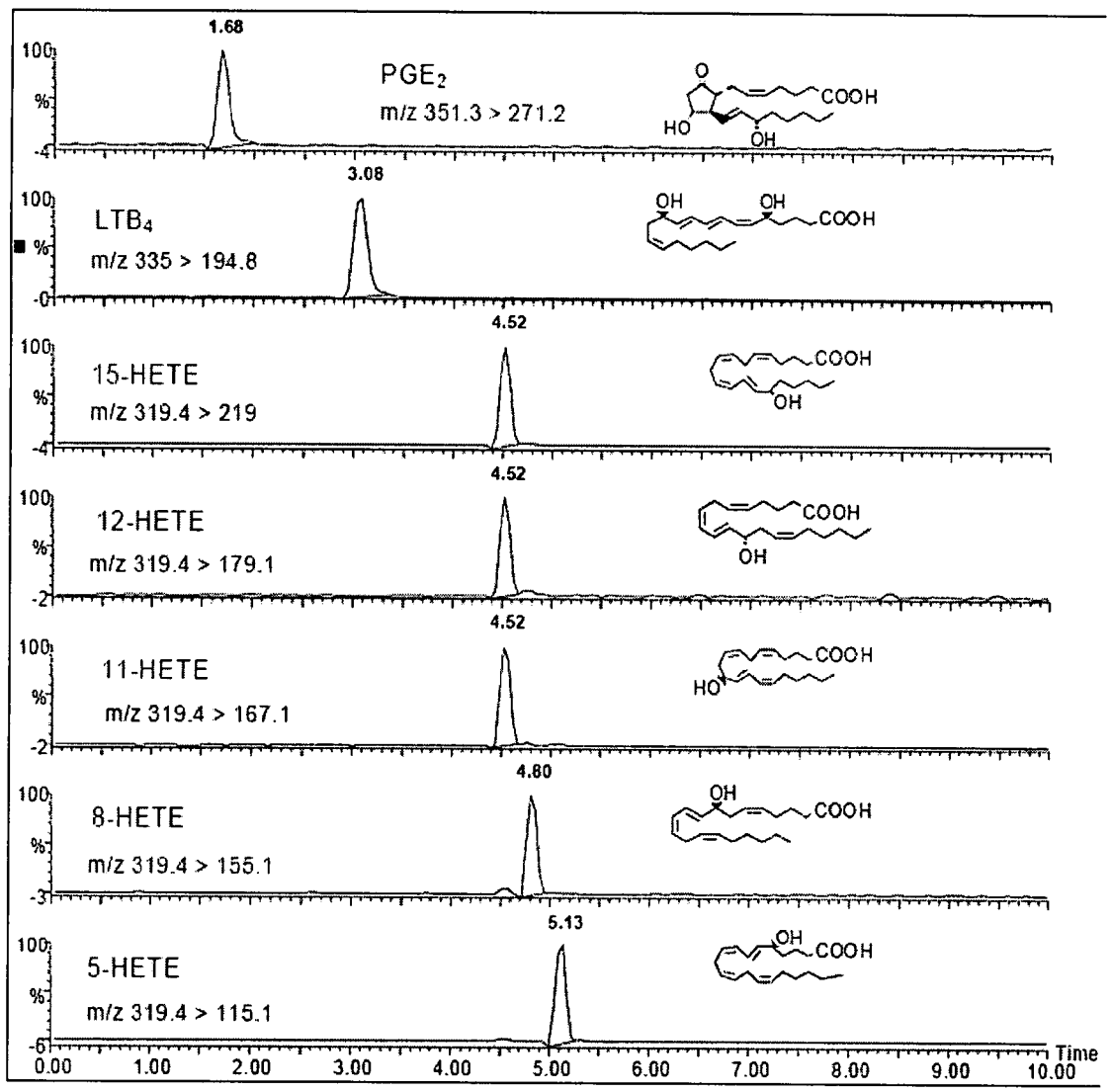
FIG. 11 is series of graphs of total ion chromatograms, which depict the analytical methodology results developed by the inventors for determination of an inflammation profile in cells and tissues. The methodology was applied to determination of eicosanoids such as PGE2 and LTB4 in the present invention. The data were obtained using Liquid Chromatography/Mass Spectrometry/Mass Spectrometry (LC/MS/MS).

The results of the "add back" experiments depicted in FIG. 10 show that the inhibition of LTB4, shown as solid black bars, is clearly evident and more pronounced than it is for either PGE2, shown as light gray hatched bar, or 5-HETE, shown as medium gray cross hatched bar. Upon treatment with 1.0 µl/ml of the inventive compositions and adding the eicosanoid LTB4 back to RBL-1 cells, the inhibition of cell growth mediated by the inventive compositions is largely overcome in a concentration dependent manner. This strongly suggests that LTB4 is important for driving cell proliferation and that the inventive compositions have a selective effect against LTB4 promotion. Conversely, adding back 5-HETE had little effect on cell growth inhibition mediated by the inventive compositions, while adding back PGE2 had a moderate effect.

Taken as a whole, these data suggest that the inventive compositions inhibit cell proliferation in a concentration dependent manner and does so through a decline in LTB4 concentrations. Adding back LTB4 largely overcomes the growth inhibition produced by the inventive compositions, suggesting again that an important mechanism of action of the inventive compositions in inhibiting the growth of these cells is to decrease cellular levels of LTB4. The data show that adding LTB4 back to RBL-1 cells reverses inhibition of cell proliferation due to the inventive compositions, and lends credence to the concept that LTB4 is important to stimulation of cell growth.

Without being bound to any particular mechanism of action, Applicants believe that oral cancer has as an etiologic factor, a high production of LTB4, which may function like a growth factor, and that the inventive compositions inhibit cell proliferation in significant part by inhibiting formation of this particular bioactive lipid.

Example 4

Effect of the Inventive Compositions on Pre-Malignant Oral Cancers

A patient presents for treatment of a low-grade or high-grade neoplasm of the oral cavity. An inventive composition is administered to said patient over a course of treatment lasting for several weeks, resulting in no significant side effects. The patient experiences a reversal in the growth of neoplastic cells and death of existing neoplastic cells, resulting in the neoplasia becoming undetectable.

Example 5

Effect of the Inventive Compositions on Oral Cancers

A patient presents for treatment of a malignant grade IV oral cancer, confirmed by manual examination and biopsy of the tumor. An inventive composition is administered to said patient over a course of treatment lasting for several months, resulting in no significant side effects. The patient experiences a reversal in the growth rate of tumor cells, death of existing tumor cells and reduction in tumor size, and no metastasis of the tumor. With continuing treatment, the patient continues to exhibit no secondary symptoms of oral cancer, no long term side effects of the treatment, and no metastasis of the tumor.

REFERENCES

The following literature references are believed to be useful to an understanding of the inventive subject matter in the context of its place in the relevant art. Citation here is not to be construed as an assertion or admission that any reference cited is material to patentability of the inventive subject matter. Applicants will properly disclose information material to patentability in an Information Disclosure Statement. The content of each reference is hereby incorporated in its entirety.

1. Li N., Sood S, Wang S, Fang M, Wang P, Sun Z, Yang C S, Chen X. Overexpression of 5-lipoxygenase and cyclooxygenase in hamster and human oral cancer and chemopreventive effects of zileuton and celecoxib. Clin. Cancer Res. 11: 2089-2096, 2005
2. Yang P, Chan D, Felix E, Madden T, Klein R D, Shureiqi I, Chen X, Dannenberg A J, Newman R A. Determination of endogenous tissue inflammation profiles by LC/MS/MS: COX- and LOX-derived bioactive lipids. Prostaglandins Leukot. Essent. Fatty Acids. Sep. 28, 2006.

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

We claim:

1. A method for treating oral cancer in a subject in need thereof, comprising the step of administering an effective amount of a composition to said subject sufficient to treat said oral cancer, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

2. The method of claim 1, wherein said composition is administered orally.

3. The method of claim 2, wherein the orally administered composition is in the form of one or more capsules, one or more tablets, or one or more pills.

4. The method of claim 1, wherein the composition comprises:
   (A) from about 4.5% to about 7.5%, and more preferably from about 5.5% to about 6.5%, by weight of the hydroalcoholic extract of ginger;
   (B) from about 5.5% to about 8.5%, and more preferably from about 6% to about 8%, by weight of the supercritical extract of ginger;
   (C) from about 1.0% to about 1.5%, and more preferably from about 1.2% to about 1.4%, by weight of the supercritical extract of turmeric;
   (D) from about 10.0% to about 16.0%, and more preferably from about 11.5% to about 14.5%, by weight of the supercritical extract of rosemary;
   (E) from about 4.0% to about 6.0%, and more preferably from about 4.5% to about 5.5%, by weight of the supercritical extract of oregano;
   (F) from about 10.0% to about 16.0%, and more preferably from about 11.5% to about 14.5%, by weight of the hydroalcoholic extract of turmeric;
   (G) from about 5.5% to about 8.0%, and more preferably from about 6.0% to about 7.0%, by weight of the hydroalcoholic extract of rosemary;
   (H) from about 10.0% to about 16.0%, and more preferably from about 11.5% to about 14.5%, by weight of the hydroalcoholic extract of holy basil;
   (I) from about 10.0% to about 16.0%, and more preferably from about 11.5% to about 14.5%, by weight of the hydroalcoholic extract of green tea;
   (J) from about 8.0% to about 12.0%, and more preferably from about 9.0% to about 11.0%, by weight of the hydroalcoholic extract of huzhang;
   (K) from about 4.0% to about 6.0%, and more preferably from about 4.5% to about 5.5%, by weight of the hydroalcoholic extract of Chinese goldthread;
   (L) from about 4.0% to about 6.0%, and more preferably from about 4.5% to about 5.5%, by weight of the hydroalcoholic extract of barberry; and
   (M) from about 2.0% to about 3.0%, and more preferably from about 2.25% to about 2.75%, by weight of the hydroalcoholic extract of *Scutellaria baicalensis*.

5. The method of claim 1, wherein the weight ratio of the supercritical extract of ginger to the hydroalcoholic extract of ginger is from about 0.8:1 to about 1.4:1.

6. The method of claim 1, wherein the weight ratio of the hydroalcoholic extract of turmeric to the supercritical extract of turmeric is from about 8:1 to about 12:1.

7. The method of claim 1, wherein the weight ratio of the supercritical extract of rosemary to the hydroalcoholic extract of rosemary is from about 1.6:1 to about 2.4:1.

8. The method of claim 1, wherein the hydroalcoholic extract of ginger comprises from about 2.4% to about 3.6% by weight of pungent compounds.

9. The method of claim 1, wherein the supercritical extract of ginger comprises from about 24% to about 36% by weight of pungent compounds and from about 6.4% to about 9.6% by weight of zingiberene.

10. The method of claim 1, wherein the supercritical extract of turmeric comprises from about 36% to about 54% by weight of turmerones.

11. The method of claim 1, wherein the supercritical extract of rosemary comprises from about 18.4% to about 27.6% by weight of total phenolic antioxidants.

12. The method of claim 1, wherein the supercritical extract of oregano comprises from about 0.64% to about 0.96% by weight of total phenolic antioxidants.

13. The method of claim 1, wherein the hydroalcoholic extract of turmeric comprises from about 5.6% to about 8.4% by weight of curcumin.

14. The method of claim 1, wherein the hydroalcoholic extract of rosemary comprises from about 18.4% to about 27.6% by weight of total phenolic antioxidants.

15. The method of claim 1, wherein the hydroalcoholic extract of holy basil comprises from about 1.6% to about 2.4% by weight of ursolic acid.

16. The method of claim 1, wherein the hydroalcoholic extract of green tea comprises from about 36% to about 54% by weight of polyphenols.

17. The method of claim 1, wherein the hydroalcoholic extract of huzhang comprises from about 6.4% to about 9.6% by weight of resveratrol.

18. The method of claim 1, wherein the hydroalcoholic extract of Chinese goldthread comprises from about 4.8% to about 7.2% by weight of berberine.

19. The method of claim 1, wherein the hydroalcoholic extract of barberry comprises from about 4.8% to about 7.2% by weight of berberine.

20. The method of claim 1, wherein said composition provided in step (a) comprises:
   (A) from about 4.5% to about 7.5% by weight of the hydroalcoholic extract of ginger, wherein the extract comprises from about 2.4% to about 3.6% by weight of pungent compounds;
   (B) from about 5.5% to about 8.5% by weight of the supercritical extract of ginger, wherein the extract comprises from about 24% to about 36% by weight of pungent compounds and from about 6.4% to about 9.6% by weight of zingiberene;
   (C) from about 1.0% to about 1.5% by weight of the supercritical extract of turmeric, wherein the extract comprises from about 36% to about 54% by weight of turmerones;
   (D) from about 10.0% to about 16.0% by weight of the supercritical extract of rosemary, wherein the extract comprises from about 18.4% to about 27.6% by weight of total phenolic antioxidants;
   (E) from about 4.0% to about 6.0% by weight of the supercritical extract of oregano, wherein the extract comprises from about 0.64% to about 0.96% by weight of total phenolic antioxidants;

(F) from about 10.0% to about 16.0% by weight of the hydroalcoholic extract of turmeric, wherein the extract comprises from about 5.6% to about 8.4% by weight of curcumin;
(G) from about 5.5% to about 8.0% by weight of the hydroalcoholic extract of rosemary, wherein the extract comprises from about 18.4% to about 27.6% by weight of total phenolic antioxidants;
(H) from about 10.0% to about 16.0% by weight of the hydroalcoholic extract of holy basil, wherein the extract comprises from about 1.6% to about 2.4% by weight of ursolic acid;
(I) from about 10.0% to about 16.0% by weight of the hydroalcoholic extract of green tea, wherein the extract comprises from about 36% to about 54% by weight of polyphenols;
(J) from about 8.0% to about 12.0% by weight of the hydroalcoholic extract of huzhang, wherein the extract comprises from about 6.4% to about 9.6% by weight of resveratrol;
(K) from about 4.0% to about 6.0% by weight of the hydroalcoholic extract of Chinese goldthread, wherein the extract from about 4.8% to about 7.2% by weight of berberine;
(L) from about 4.0% to about 6.0% by weight of the hydroalcoholic extract of barberry, wherein the extract from about 4.8% to about 7.2% by weight of berberine; and
(M) from about 2.0% to about 3.0% by weight of the hydroalcoholic extract of *Scutellaria baicalensis;*
and wherein said composition further comprises:
(i) the supercritical extract of ginger and the hydroalcoholic extract of ginger at a weight ratio of from about 0.9 to about 1.4 parts of supercritical extract per 1 part of post supercritical hydroalcoholic extract;
(ii) the hydroalcoholic extract of turmeric and the supercritical extract of turmeric at a weight ratio of from about 8 to about 12 parts of hydroalcoholic extract per 1 part of supercritical extract; and
(iii) the supercritical extract of rosemary and the hydroalcoholic extract of rosemary at a weight ratio of from about 1.6 to about 2.4 parts of supercritical extract per 1 part of hydroalcoholic extract.

21. The method of claim 1, said composition is administered in a daily dosage of at least about 700 mg.

22. The method of claim 1, wherein said composition is administered on a daily basis for at least 4 weeks.

23. A method for treating at least one cancerous tumor of the oral cavity in a subject in need thereof, comprising the step of administering an effective amount of a composition to said subject sufficient to treat said tumor, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

24. The method of claim 23, wherein said composition is administered orally.

25. The method of claim 24, wherein the orally administered composition is in the form of one or more capsules, one or more tablets, or one or more pills.

26. The method of claim 23, wherein the composition comprises:
(A) from about 4.5% to about 7.5%, and more preferably from about 5.5% to about 6.5%, by weight of the hydroalcoholic extract of ginger;
(B) from about 5.5% to about 8.5%, and more preferably from about 6% to about 8%, by weight of the supercritical extract of ginger;
(C) from about 1.0% to about 1.5%, and more preferably from about 1.2% to about 1.4%, by weight of the supercritical extract of turmeric;
(D) from about 10.0% to about 16.0%, and more preferably from about 11.5% to about 14.5%, by weight of the supercritical extract of rosemary;
(E) from about 4.0% to about 6.0%, and more preferably from about 4.5% to about 5.5%, by weight of the supercritical extract of oregano;
(F) from about 10.0% to about 16.0%, and more preferably from about 11.5% to about 14.5%, by weight of the hydroalcoholic extract of turmeric;
(G) from about 5.5% to about 8.0%, and more preferably from about 6.0% to about 7.0%, by weight of the hydroalcoholic extract of rosemary;
(H) from about 10.0% to about 16.0%, and more preferably from about 11.5% to about 14.5%, by weight of the hydroalcoholic extract of holy basil;
(I) from about 10.0% to about 16.0%, and more preferably from about 11.5% to about 14.5%, by weight of the hydroalcoholic extract of green tea;
(J) from about 8.0% to about 12.0%, and more preferably from about 9.0% to about 11.0%, by weight of the hydroalcoholic extract of huzhang;
(K) from about 4.0% to about 6.0%, and more preferably from about 4.5% to about 5.5%, by weight of the hydroalcoholic extract of Chinese goldthread;
(L) from about 4.0% to about 6.0%, and more preferably from about 4.5% to about 5.5%, by weight of the hydroalcoholic extract of barberry; and
(M) from about 2.0% to about 3.0%, and more preferably from about 2.25% to about 2.75%, by weight of the hydroalcoholic extract of *Scutellaria baicalensis*.

27. The method of claim 23, wherein said at least one cancerous tumor is detected during surgery on the oral cavity of said subject, having not been felt by a physician on physical examination of said subject.

28. The method of claim 23, wherein said at least one cancerous tumor is confined to the oral cavity of said subject and is detected by a physician on physical examination of said subject.

29. The method of claim 23, wherein cancer related to said at least one cancerous tumor extends beyond the oral cavity of said subject, but has not spread to lymph nodes in said subject.

30. The method of claim 23, wherein cancer related to said at least one cancerous tumor is metastasized to regional lymph nodes or other parts of said subject.

31. A method for treating side effects associated with oral cancer in a subject in need thereof, comprising the step of administering an effective amount of a composition to said subject sufficient to treat said side effects, said composition comprising therapeutically effective amounts of supercritical extracts of rosemary, turmeric, oregano and ginger; and therapeutically effective amounts of hydroalcoholic extracts of holy basil, ginger, turmeric, *Scutellaria baicalensis*, rosemary, green tea, huzhang, Chinese goldthread, and barberry.

32. The method of claim 31, wherein said composition is administered orally.

33. The method of claim 32, wherein the orally administered composition is in the form of one or more capsules, one or more tablets, or one or more pills.

34. The method of claim 31, wherein the composition comprises:
- (A) from about 4.5% to about 7.5%, and more preferably from about 5.5% to about 6.5%, by weight of the hydroalcoholic extract of ginger;
- (B) from about 5.5% to about 8.5%, and more preferably from about 6% to about 8%, by weight of the supercritical extract of ginger;
- (C) from about 1.0% to about 1.5%, and more preferably from about 1.2% to about 1.4%, by weight of the supercritical extract of turmeric;
- (D) from about 10.0% to about 16.0%, and more preferably from about 11.5% to about 14.5%, by weight of the supercritical extract of rosemary;
- (E) from about 4.0% to about 6.0%, and more preferably from about 4.5% to about 5.5%, by weight of the supercritical extract of oregano;
- (F) from about 10.0% to about 16.0%, and more preferably from about 11.5% to about 14.5%, by weight of the hydroalcoholic extract of turmeric;
- (G) from about 5.5% to about 8.0%, and more preferably from about 6.0% to about 7.0%, by weight of the hydroalcoholic extract of rosemary;
- (H) from about 10.0% to about 16.0%, and more preferably from about 11.5% to about 14.5%, by weight of the hydroalcoholic extract of holy basil;
- (I) from about 10.0% to about 16.0%, and more preferably from about 11.5% to about 14.5%, by weight of the hydroalcoholic extract of green tea;
- (J) from about 8.0% to about 12.0%, and more preferably from about 9.0% to about 11.0%, by weight of the hydroalcoholic extract of huzhang;
- (K) from about 4.0% to about 6.0%, and more preferably from about 4.5% to about 5.5%, by weight of the hydroalcoholic extract of Chinese goldthread;
- (L) from about 4.0% to about 6.0%, and more preferably from about 4.5% to about 5.5%, by weight of the hydroalcoholic extract of barberry; and
- (M) from about 2.0% to about 3.0%, and more preferably from about 2.25% to about 2.75%, by weight of the hydroalcoholic extract of *Scutellaria baicalensis*.

* * * * *